(12) United States Patent
Coch et al.

(10) Patent No.: US 11,110,124 B2
(45) Date of Patent: Sep. 7, 2021

(54) CELL DERIVED EXTRACELLULAR VESICLES FOR THE TREATMENT OF DISEASES

(71) Applicant: Rheinische Friedrich-Wilhelms-Universitaet Bonn, Bonn (DE)

(72) Inventors: Christoph Coch, Bonn (DE); Juliane Dassler-Plenker, Bonn (DE); Gunther Hartmann, Bonn (DE)

(73) Assignee: RHEINISCHE FRIEDRICH-WILHELMS-UNIVERSITAET BONN, Bonn (DE)

( * ) Notice: Subject to any disclaimer, the term of this patent is extended or adjusted under 35 U.S.C. 154(b) by 185 days.

(21) Appl. No.: 16/049,136

(22) Filed: Jul. 30, 2018

(65) Prior Publication Data

US 2019/0030072 A1  Jan. 31, 2019

(30) Foreign Application Priority Data

Jul. 31, 2017 (EP) .................................... 17184033

(51) Int. Cl.
| | |
|---|---|
| *A61K 39/00* | (2006.01) |
| *A61K 35/17* | (2015.01) |
| *A61P 37/04* | (2006.01) |
| *A61K 35/33* | (2015.01) |
| *A61P 35/00* | (2006.01) |
| *C07K 14/705* | (2006.01) |
| *A61K 35/13* | (2015.01) |
| *C12N 5/09* | (2010.01) |
| *A61K 35/12* | (2015.01) |
| *C12N 15/11* | (2006.01) |

(52) U.S. Cl.
CPC .............. *A61K 35/17* (2013.01); *A61K 35/12* (2013.01); *A61K 35/13* (2013.01); *A61K 35/33* (2013.01); *A61K 39/0011* (2013.01); *A61P 35/00* (2018.01); *A61P 37/04* (2018.01); *C07K 14/705* (2013.01); *C12N 5/0693* (2013.01); *C12N 15/11* (2013.01); *A61K 2035/122* (2013.01); *A61K 2039/55555* (2013.01); *C12N 2501/65* (2013.01); *C12N 2502/11* (2013.01); *C12N 2502/1157* (2013.01); *C12N 2502/1164* (2013.01); *C12N 2502/1178* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 2017/0143812 A1 | 5/2017 | Ichim et al. | |
| 2019/0062710 A1* | 2/2019 | Betancourt | ............ A61K 35/12 |

FOREIGN PATENT DOCUMENTS

| | | |
|---|---|---|
| WO | 2011/000551 A1 | 1/2011 |
| WO | 2015/058148 A1 | 4/2015 |

OTHER PUBLICATIONS

Dassler-Plenker et al (OncoImmunol, 2016, v.5 p. 1-11.*
Damo et al ( Scientific Report,2015,v.5, p. 1-430);.*
Reiners et at ( Blood, 2013,v. 121,pp. 3658-3665).*
Viaud et al., "Updated Technology to Produce Highly Immunogenic Dendritic Cell-derived Exosomes of Clinical Grade: A Crititcal Role of Interferon-γ", J Immunother , Jan. 1, 2011, vol. 34, No. 1, pp. 65-75.
Guo et al., "Exosomes: New players in cancer (Review)", Oncology Reports, 2017, vol. 38, pp. 665-675.
Besse et al., "Dendritic cell-derived exosomes as maintenance immunotherapy after first line chemotherapy in NSCLC", OncoImmunology, 2016, vol. 5, No. 4, e1071008, 13 pages.
Pitt et al., "Dendritic cell-derived exosomes for cancer therapy", The Journal of Clinical Investigation, Apr. 2016, vol. 126, No. 4, pp. 1224-1232.
Daβler-Plenker et al., "RIG-I activation induces the release of extracellular vesicles with antitumor activity", OncoImmunology, 2016, vol. 5, No. 10, e1219827, 11 pages.

* cited by examiner

*Primary Examiner* — Michail A Belyavskyi
(74) *Attorney, Agent, or Firm* — MH2 Technology Law Group, LLP

(57) ABSTRACT

The present invention pertains to extracellular vesicles (exosomes) that are produced by culturing tumor cells in the presence of various ligands or activators of innate immunity receptors and subsequently isolating and purifying the vesicles in the culture supernatant. The invention provides also pharmaceutical compositions comprising the inventive exosomes. The exosomes of the invention are provided as medicaments for example in the treatment of cancer diseases.

11 Claims, 17 Drawing Sheets

Figure 1:
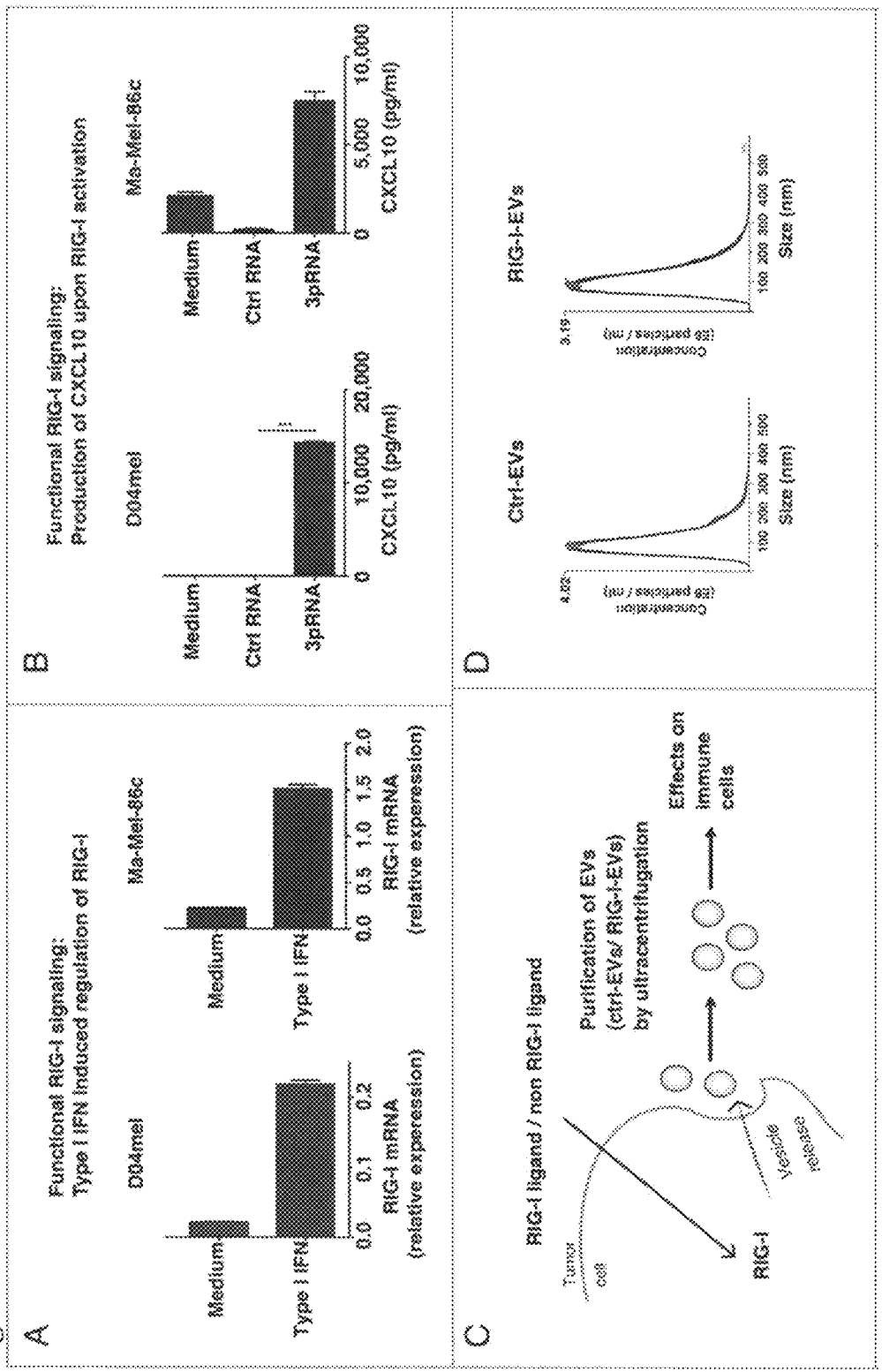

Specification includes a Sequence Listing.

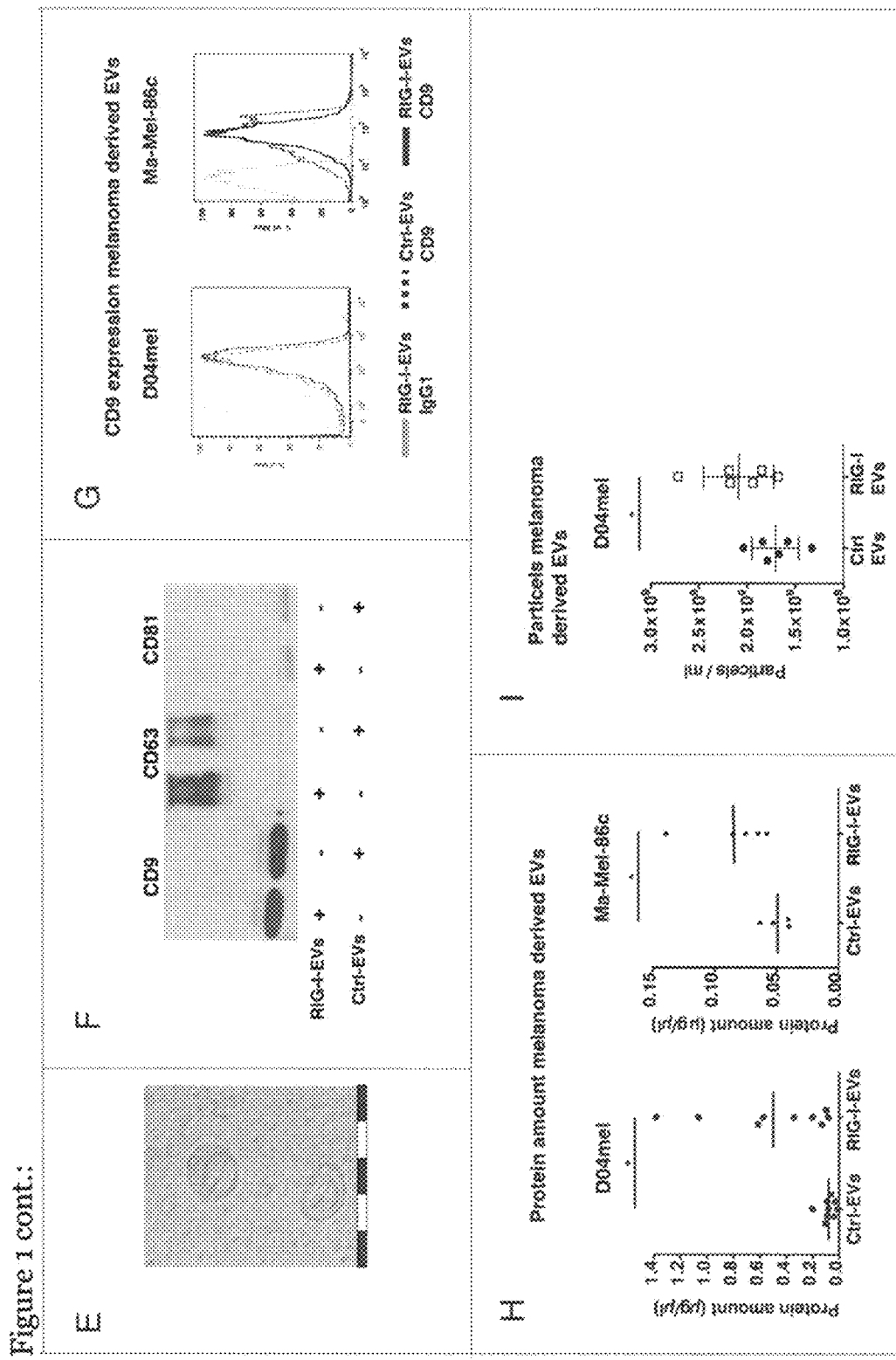

C

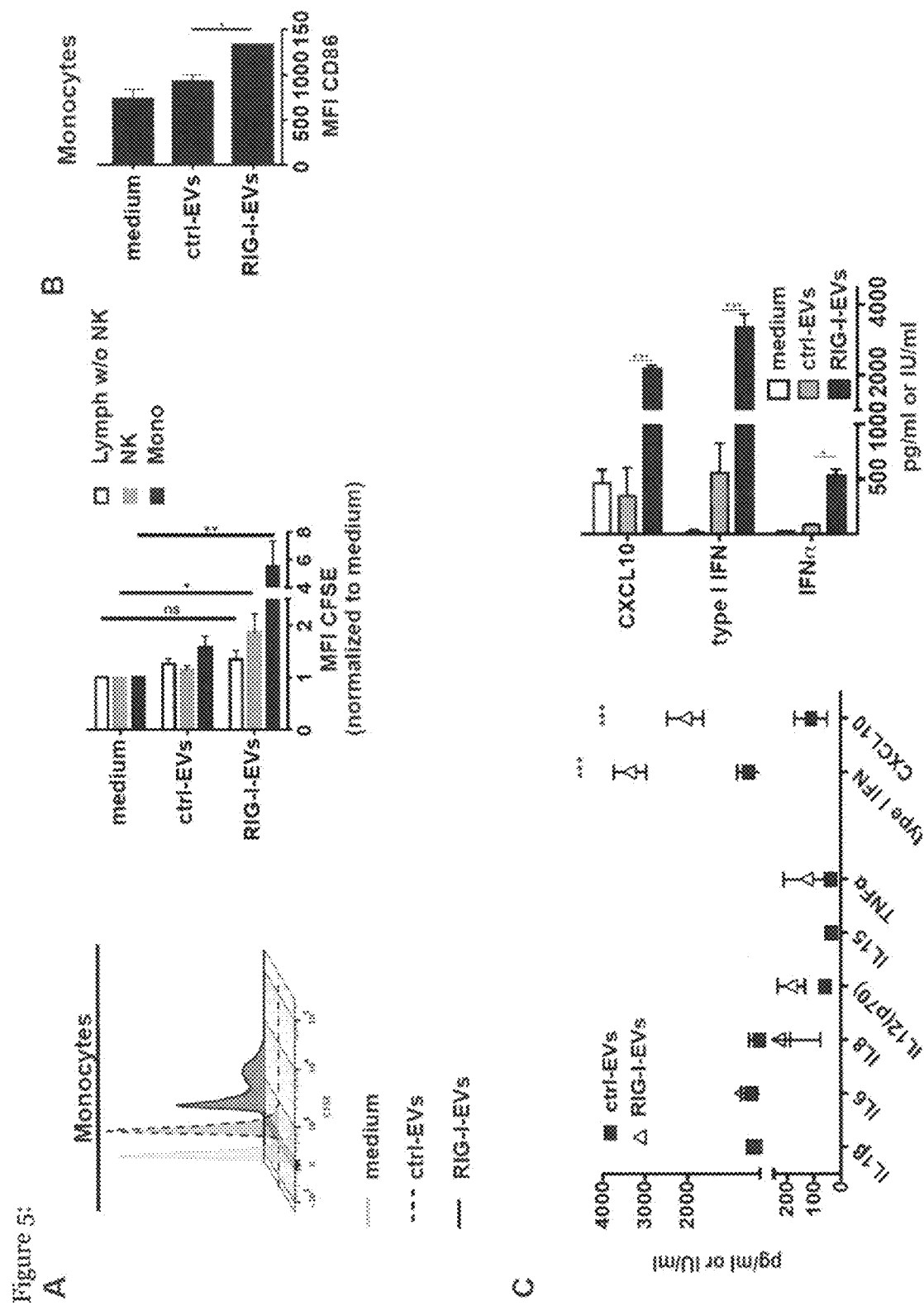

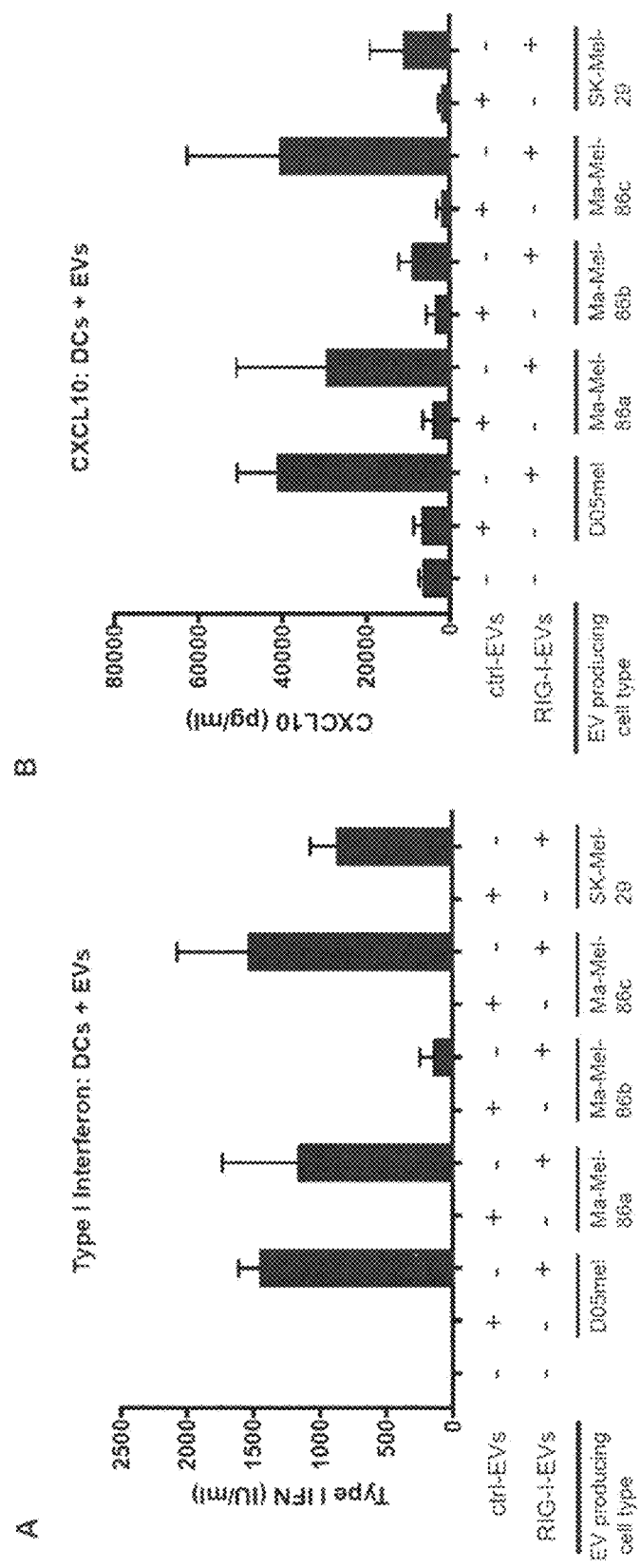

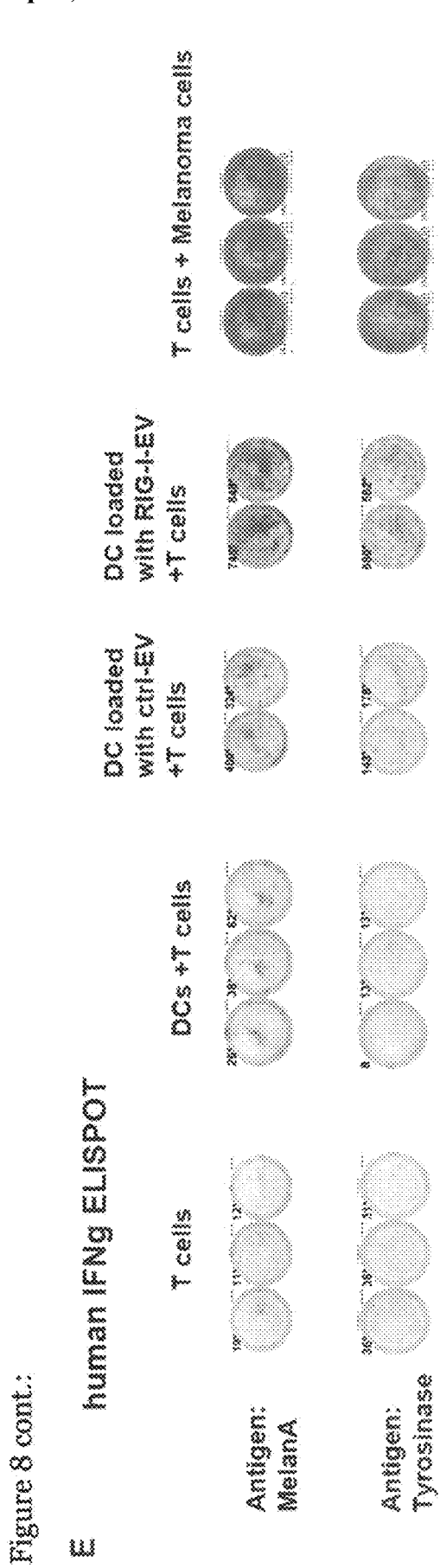

CELL DERIVED EXTRACELLULAR VESICLES FOR THE TREATMENT OF DISEASES

CROSS-REFERENCE TO RELATED APPLICATION

This application claims priority to and the benefit of European Patent Application No. 17184033.3, filed 31 Jul. 2017, the entire contents of which are herein incorporated by reference.

SEQUENCE LISTING

The instant application contains a Sequence Listing which has been submitted electronically in ASCII format and is hereby incorporated by reference in its entirety. Said ASCII copy, created on 27 Jul. 2018, is named 0355_0003_Sequence_Listing.txt and is 3 Kilobytes in size.

FIELD OF THE INVENTION

The present invention pertains to extracellular vesicles (including exosomes) that are produced by culturing biological cells such as tumor cells or fibroblasts in the presence of various ligands or activators of innate immunity receptors and subsequently isolating and purifying the vesicles in the culture supernatant. The invention provides also pharmaceutical compositions comprising the inventive extracellular vesicles. The extracellular vesicles of the invention are provided as medicaments for example in the treatment of cancer or viral diseases.

DESCRIPTION

Over the last years, communication by extracellular vesicles (EVs), e.g., exosomes, emerged as an important mechanism in regulating intercellular crosstalk. EVs are released by a multitude of malignant and non-malignant cells including melanoma cells. Depending on the EV releasing cell type, they can transfer several functional active molecules between cells inducing different effects in the recipient cell. EVs derived from immune cells are described to enhance antitumor immunity. Dendritic cell (DC)-derived exosomes have the ability to activate NK cells against tumors leading to their evaluation in tumor therapy. Clinical impact of NK cell activating DC-derived exosomes was recently documented in a Phase II trial in NSCLC stage IV patients. In a fraction of patients presenting with defective NKp30 expression prolonged progression-free survival was associated with enhanced NKp30-dependent NK cell functions correlating with MHCII and BAG6 expression levels on exosomes. BAG6 is an inducible surface ligand that binds to the activating natural cytotoxicity receptor NKp30 on NK cells. Furthermore, BAG6-positive EVs have been identified as important regulators of NK cell activity. In contrast to immune cell-derived EVs, it has been shown that tumor-derived EV (e.g., from melanoma) induce tolerance and thus strongly promote tumor growth and metastasis by a variety of different mechanisms, including the induction of an immunosuppressive environment. Consequently, targeting of EVs has been suggested as a therapeutic strategy for the treatment of tumors. However, there are only few experimental studies on the mechanisms how tumor-exosomes can be actively turned against the tumor.

There is emerging evidence that an antiviral immune response can induce changes in the composition and the function of EVs. For example, HCV-infected cells release exosomes containing viral components triggering an innate immune response. Still, little is known about the impact of innate immune sensing receptors, initially responding to the viral infection, on the formation and function of EVs. Retinoic acid-inducible gene I (RIG-I) is a cytosolic immune sensing receptor detecting viral 5'-triphosphorylated RNA. Unlike toll-like receptors (TLR), RIG-I is expressed in all nucleated cells, including tumor cells (e.g., melanoma cells). Therapeutic stimulation of RIG-I with a synthetic 5'-triphosphate RNA oligonucleotide (3pRNA) induced a potent antitumor immune response mediated by NK cells and myeloid cells. The mechanism by which NK cells are directed to specifically kill 3pRNA-treated tumor cells remains unknown.

Many therapeutic approaches in the prior art suggest the use of extracellular vesicles such as exosomes in the treatment of various diseases. Therefore, it was an object of the present invention to provide a method for the generation of improved extracellular vesicles that can be applied in medicine.

The above problem is solved in a first aspect by a method for the production of extracellular vesicles comprising a step of contacting a biological cell with at least one ligand of an innate immunity receptor.

The above problem is solved in a first embodiment of the first aspect by a method for the production of extracellular vesicles, which preferably harbor an antiinfective and/or anti-tumor activity and/or immune-stimulatory activity, wherein the method comprises the steps of
  (a) In vitro culturing a biological cell,
  (b) Bringing into contact the biological cell with at least one ligand of an innate immunity receptor in an amount and time sufficient for the biological cell to release extracellular vesicles,
  (c) Isolating and/or purifying the released extracellular vesicles.

The term "extracellular vesicle" in context of the present invention shall be understood to refer to a small (smaller than a biological cell) sphere surrounded by a membrane which originated from a biological cell. This sphere varies greatly depending on the origins of the cells in which it is made or the way it is made. In this invention, the sphere includes any one selected from the group consisting of exosome, ectosome, microvesicle, and apoptotic body, and preferably is an exosome.

In a preferred embodiment of the present invention the biological cell expresses at least one innate immunity receptor, either endogenously or via a transgene. The transgene encoding for an innate immunity receptor, for example, might be introduced and expressed in the biological cell by standard methods in the art in advance before performing step (b) of the method of the invention. In preferred embodiments of the invention an "innate immunity receptor" is any receptor able to bind a pattern recognition receptor ligands of the innate immune system, e.g. RIG-I like receptors, DNA recognizing receptors, Toll-like receptors (TLR).

The term "biological cell" in context of the invention may refer to any biological cell of a vertebrate, preferably a mammal such as mice, rats, dogs, cats, monkey or other domesticated mammalian animals, and most preferably a biological cell is a human cell. Also, the biological cell is in some embodiments selected from a tumor cell, or a non-tumor cell. A non-tumor cell is preferably an epithelial cell, an immune cell or a fibroblast. In some additional or alternative embodiments, the biological cell is a cell which is devoid of a Major Histocompatibility Complex (MHC), class I and/or II. EVs derived from such biological cells which do not express or comprise MHC class I and/or II are preferable because the EVs as such will not be the target for the T cell mediated immune response themselves.

The released extracellular vesicles produced according to the method of the invention comprises (therefore includes in its membrane and/or vesicle lumen) at least one ligand of an innate immunity receptor. Furthermore, the use of the innate immunity receptor ligands for a stimulation of cells to produce extracellular vesicles surprisingly leads to the introduction of the innate immune receptor ligand together with various antigens into the extracellular vesicle produced according to the invention. Hence, the released extracellular vesicles produced according to the method of the invention comprises (therefore includes in its membrane and/or vesicle lumen) antigens derived from said biological cell together with the innate immunity ligands, which is advantageous. Such antigens preferably are tumor associated antigens (TAA) or tumor specific antigens (TSA).

In some preferred embodiments of the invention TAA or TSA are introduced into the biological cell exogenously. For example the invention may comprise a step of transfecting one or more TAA and/or TSA into the biological cell, either as protein or as a TAA or TSA encoding nucleic acid expression construct. In this embodiment the EVs of the invention will also comprise the so introduced TAA and/or TSA.

As mentioned before, the extracellular vesicles (EV) of the invention harbor advantageous anti-infective and/or anti-tumor activity. Preferably these activities involve an activity of inducing cytokine production, and/or the extra-cellular vesicles to activate immune cells, such as monocytes, dendritic cells, natural killer (NK) cells and/or T cells. Furthermore, the EVs produced according to the method of the invention have surprisingly strong immune stimulatory effects, which partly overlap or supplement the above anti-infective and/or anti-tumor activity. In some embodiments it shall be understood that when the EVs of the invention are derived from a tumor cell as biological cell, the EVs harbors in particular anti-tumor activity. On the other hand, in further embodiments, anti-infective EVs of the invention may be produced using non-tumor cells as biological cells.

The term "anti-infective" is used throughout the description to describe a biologically activity for augmenting or supporting the killing or inhibition of the growth of certain harmful pathogenic organisms, including but not limited to bacteria, yeasts and fungi, viruses, protozoa or parasites. Preferably the anti-infective activity in context of the invention is an anti-viral activity.

In certain embodiments the at least one ligand of an innate immunity receptor is selected from the group consisting of ligand of retin-oic acid-inducible gene I (RIG-I), ligand of melanoma differentiation antigen 5 (MDA5) and ligand of cyclic GMP-AMP synthase (cGAS); and preferably is an RNA molecule, such as 3pRNA, a DNA molecule, such as Y-form DNA, or is polyinosinic:polycytidylic acid poly (I:C). Respectively, in alternative or additional embodiments the at least one innate immunity receptor is retinoic acid-inducible gene I (RIG-I), melanoma differentiation antigen 5 (MDA5) and/or is cyclic GMP-AMP synthase (cGAS).

In some embodiments the biological cell is derived from isolated tissue, such as dissected tissue. Such tissue or isolated cell in some embodiments is stored for longer periods, for example more than 4 hours, for example by freezing. Alternatively, in some other embodiments the dissected tissue is not frozen or stored for periods longer than 2 to 5 days (fresh tissue).

In some embodiments of the invention it is preferred that step (b) of the inventive method comprises bringing into contact the biological cell with at least two ligands of an innate immunity receptor selected from the group consisting of an RNA molecule, such as 3pRNA, a DNA molecule, such as Y-form DNA, and polyinosinic:polycytidylic acid poly (I:C); and wherein the at least two ligands of an innate immunity receptor are two ligands of two different innate immunity receptors.

Yet another embodiment of the invention then pertains to a method, wherein step (b) comprises bringing into contact the biological cell with at least three ligands of an innate immunity receptor selected from the group consisting of an RNA molecule, such as 3pRNA, a DNA molecule, such as Y-form DNA, and polyinosinic:polycytidylic acid poly (I:C); and wherein the at least three ligands of an innate immunity receptor are three ligands of three different innate immunity receptors.

Correspondingly, other embodiments of the invention relate to the method of the invention wherein the tumor cell expresses at least two, preferably three, innate immunity receptors selected from the group consisting of retinoic acid-inducible gene I (RIG-I), melanoma differentiation anti-gen 5 (MDA5) and is cyclic GMP-AMP synthase (cGAS).

Further embodiments of the invention relate to a method, wherein the at least one ligand of an innate immunity receptor is brought into contact with the biological cell by introducing into the biological cell the protein of the at least one ligand of an innate immunity receptor, or alternatively by introducing into the biological cell an expression construct of the at least one ligand of an innate immunity receptor and expressing said at least one ligand of an innate immunity receptor via the expression construct in the biological cell for a time period sufficient for the biological cell to release extra-cellular vesicles. Such methods of introducing whole proteins or expression constructs into biological cells are well known to the skilled artisan.

In some embodiments the biological cell is a tumor cell isolated from a tumor sample of a patient suffering from a tumor disease. EVs produced according to this embodiment may preferably be used in the therapy of the respective patient from whom the tumor sample was obtained.

In embodiments of the invention where the biological cell is a tumor cell, the biological cell is preferably a melanoma cell, most preferably a human melanoma cell.

The method of the invention in preferred embodiments shall include a step of purifying and/or isolating the EVs of the invention. Preferably, the isolating and/or purifying comprises a step of separating the biological cell and the culture medium (supernatant). However, in the art many methods for the purification and isolation of EVs of various kinds are known and the invention shall not be restricted to any one of them.

However, in some embodiments the inventive method comprises an isolating and/or purifying which includes a step of determining the presence of BAG6 on or in the extracellular vesicles. In these instances it may be preferred that isolating and/or purifying comprises a further step of purifying/isolating extracellular vesicles which comprise BAG6. In this embodiment the BAG6 positive EVs are enriched/concentrated.

As mentioned before, in certain embodiments it might be advantageous that the method comprises an additional step of enriching/concentrating the extracellular vesicles.

The aforementioned problem is furthermore solved by a method of producing a medicament for treating a disease in a patient, the method comprising the steps of
(a) Providing a biological cell,
(b) performing with the biological cell the method for producing EVs as described before, to obtain released EVs with anti-infective and/or anti-tumor activity,
(c) formulating a medicament with the released anti-tumor extracellular vesicles for treating a disease in a patient.

In certain embodiments the medicament produced according to the invention is a vaccine. The inventors surprisingly found that EVs produced according to the methods of the invention harbor many antigens that lead to a specific activation of a T cell mediated immune response together with the innate immunity receptor ligands used for the generation of the EVs. Therefore, the medicament of the invention can be used as an improved vaccine, in particular a tumor vaccine if the EVs are derived from a tumor cell.

The step of formulating a medicament with the released anti-tumor extracellular vesicles for treating a disease in a patient of the method of invention comprises preferably a step of producing a composition of the EVs with at least one pharmaceutically acceptable carrier and/or excipient. More preferably the step might include forming a composition with the EVs and at least one pharmaceutically acceptable carrier and/or excipient which is preferably used to formulate membrane vesicles. Such carriers and/or excipients are well known in the art.

In some embodiments the biological cell is derived from a cellular sample of a patient to be treated, and wherein the formulated medicament is for treating said patient. This embodiment pertains to medicaments for use in an autologous EV therapy of a patient suffering from a disease. In this setting the EVs obtained from cells of the patient are used to treat the very same patient, which often might be preferably to avoid adverse immune reactions during therapy.

However, other embodiments of the invention relate to methods for the production of a medicament, wherein the biological cell is not derived from the patient to be treated. This embodiment relates to a heterologous use of EVs in therapy.

The terms "sample" or "cellular sample" shall in any case refer to a sample of an individual subject comprising biological cells of any kind. A sample of the invention can be a liquid or a solid (tissue) sample. Preferred samples are blood samples, or serum or plasma samples. Tissue samples may be derived from any organ of an organism or is preferably a tissue sample of a tumorous tissue.

The medicaments comprising the EVs of the invention may be used for the treatment of many different disorders. Which disease or disorder is treated will be dependent on the origin of the biological cell used in the generation of EVs according to the invention. For example it is advantageous to use tumor cell derived EVs and medicaments formulated therewith, in the treatment of a tumor disease, and preferably of the tumor diseases from which the EVs were produced.

However, it shall be understood that EVs produced from other cell types, such as healthy immune- or fibroblast cells harbor similarly advantageous medical effects as cells derived from diseased tissue such as tumors. Hence, the method of the invention in some embodiments includes a disease which is a non-tumor disease, such as a viral disease, and wherein the biological cell is a non-tumor cell, such as a fibroblast or immune cell.

The methods of the invention may in some embodiments be preferably carried out in vitro or ex vivo.

Another aspect of the invention then provides a method for treating a disease in a patient (or subject), the method comprising the steps of
(a) performing the method for the production of EVs as described before to obtain released extracellular vesicles with an anti-infective and/or anti-tumor activity,
(b) administering to the patient (or subject) the released extracellular vesicles obtained in (a) in a therapeutically effective amount to treat the disease in the patient.

A treatment according to the present invention preferably involves an immune stimulation, preferably an immune stimulation of a tumor microenvironment.

In some embodiments of the treatment of the invention, the disease is cancer, and correspondingly the biological cell is a tumor cell.

In other embodiments wherein the disease is a viral disease, the biological cell is a non-tumor cell, such as an immune cell an epithelial cell, or a fibroblast.

The treatment method according to the invention may comprise prior to step (a) the additional steps of:
(i) Obtaining a sample of the patient containing biological cells,
(ii) Isolating from the sample at least one biological cell.

A cancer disease according to the invention is preferably selected from any type of cancer or neoplasm or malignant tumor found in mammals, including carcinomas and sarcomas, such as cancer of the brain, breast, cervix, colon, head & neck, kidney, lung, non-small cell lung, melanoma, mesothelioma, ovary, sarcoma, stomach, uterus and medulloblastoma, as well as any form blood forming cancer, such as leukemia or lymphoma.

In another aspect the invention also provides an isolated extracellular vesicle obtainable by/or obtained by a method for the production of EVs as described herein above.

Further provided is a pharmaceutical composition comprising the isolated extracellular vesicle of the invention, together with at least one pharmaceutically acceptable carrier and/or excipient.

The pharmaceutical composition of the invention is formulated to be compatible with its in-tended route of administration. Examples of routes of administration include parenteral, e.g., intrathecal, intra-arterial, intravenous, intradermal, subcutaneous, oral, transdermal (topical), intracerebroventricular, intraparenchymal, intratumoral and transmucosal administration.

The term "intrathecal," as used herein, means introduced into or occurring in the space under the arachnoid membrane which covers the brain and spinal cord. The term "intracerebroventricular" refers to administration of a composition into the ventricular system of the brain, e.g., via injection, infusion, or implantation (for example, into a ventricle of the brain). As used herein, the term "intraparenchymal" can refer to an administration directly to brain tissue. In other instances, intraparenchymal administration may be directed to any brain region where delivery of one or more compounds of the invention is effective to mitigate or prevent one or more of disorders as described herein. Forms of administration directly to brain tissue is on some embodiments preferred.

Solutions or suspensions used for parenteral, intradermal, or subcutaneous application can include the following components: a sterile diluent such as water for injection, saline solution, fixed oils, polyethylene glycols, glycerine; propylene glycol or other synthetic solvents; anti-bacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the injectable composition should be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a sulfotransferase inhibitor) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Stertes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the pharmaceutical compositions are formulated into ointments, salves, gels, or creams as generally known in the art.

In certain embodiments, the pharmaceutical composition is formulated for sustained or controlled release of the active ingredient. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from e.g. Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art.

It is especially advantageous to formulate oral or parenteral compositions in dosage unit form for ease of administration and uniformity of dosage. Dosage unit form as used herein includes physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of ad-ministration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. The pharmaceutical compositions can be included in a container, pack, or dispenser together with instructions for administration.

In some specific embodiments the invention is defined by the following set of items:

Item 1. An in vitro method for the production of extracellular vesicles with an anti-infective and/or anti-tumor activity and/or immune stimulatory activity, the method comprising the steps of
(a) In vitro culturing a biological cell,
(b) Bringing into contact the biological cell with at least one ligand of an innate immunity receptor in an amount and time sufficient for the biological cell to release extracellular vesicles,
(c) Isolating and/or purifying the released extracellular vesicles.

Item 2. The method according to item 1, wherein the biological cell is selected from a tumor cell, or a non-tumor cell, such as, an epithelial cell, an immune cell or a fibroblast.

Item 3. The method according to any one of items 1 or 2, wherein the anti-infective and/or anti-tumor activity and/or immune stimulatory activity involves an activity of inducing cytokine production, and/or an activity of the extracellular vesicles to activate immune cells, such as monocytes, natural killer (NK) cells and/or T cells.

Item 4. The method according to any one of items 1 to 3, wherein the at least one ligand of an innate immunity receptor is selected from the group consisting of ligand of retinoic acid-inducible gene I (RIG-I), ligand of melanoma differentiation antigen 5 (MDA5) and ligand of cyclic GMP-AMP synthase (cGAS); and preferably is an RNA molecule, such as 3pRNA, a DNA molecule, such as Y-form DNA, or is poly-inosinic:polycytidylic acid poly (I:C).

Item 5. The method according to any one of items 1 to 4, wherein the at least one innate immunity receptor is retinoic acid-inducible gene I (RIG-I), melanoma differentiation antigen 5 (MDA5) and/or is cyclic GMP-AMP synthase (cGAS).

Item 6. The method according to any one of items 1 to 5, wherein isolating and/or purifying comprises a step of determining the presence of BAG6 on the extracellular vesicles.

Item 7. The method according to any one of items 1 to 6, wherein step (b) comprises bring-ing into contact the biological cell with at least two ligands of an innate immunity receptor selected from the group consisting of an RNA molecule, such as 3pRNA, a DNA molecule, such as Y-form DNA, and polyinosinic:polycytidylic acid poly (I:C); and wherein the at least two ligands of an innate immunity receptor are two ligands of two different innate immunity receptors.

Item 8. The method according to any one of items 1 to 7, wherein step (b) comprises bring-ing into contact the biological cell with at least three ligands of an innate immunity receptor selected from the group consisting of an RNA molecule, such as 3pRNA, a DNA molecule, such as Y-form DNA, and polyinosinic:polycytidylic acid poly (I:C); and wherein the at least three ligands of an innate immunity receptor are three ligands of three different innate immunity receptors.

Item 9. A method of producing a medicament for treating a disease in a patient, the method comprising the steps of
(a) Providing a biological cell,
(b) Performing with the biological cell the method according to any one of items 1 to 9, to obtain released extracellular vesicles with anti-infective and/or anti-tumor activity and/or immune stimulatory activity,
(c) Formulating a medicament with the released anti-tumor extracellular vesicles for treating a disease in a patient.

Item 10. The method according to item 10, wherein the biological cell is derived from a cellular sample of a patient to be treated, and wherein the formulated medicament is for treating said patient.

Item 11. The method according to item 10, wherein the biological cell is not derived from the patient to be treated.

Item 12. The method according to any one of items 10 to 12, wherein the disease is cancer, and wherein the biological cell is a tumor cell; or wherein the disease is a viral disease, and wherein the biological cell is a fibroblast.

Item 13. An extracellular vesicle for use in a method for treating a disease in a patient, the method comprising the steps of
(a) Performing the method according to any one of items 1 to 9 to obtain re-leased extracellular vesicles with an anti-infective and/or anti-tumor activity and/or immune stimulatory activity,
(b) Administering to the patient the released extracellular vesicles obtained in (a) in a therapeutically effective amount to treat the disease in the patient.

Item 14. The extracellular vesicle for use according to item 13, wherein the biological cell is derived from the patient to be treated (autologous treatment), or wherein the biological cell is not derived from the patient to be treated (heterologous treatment).

Item 15. An isolated extracellular vesicle obtainable by/or obtained by a method according to any one of items 1 to 9.

Item 16. A pharmaceutical composition comprising the isolated extracellular vesicle according to item 15, together with at least one pharmaceutically acceptable carrier and/or excipient.

The present invention will now be further described in the following examples with reference to the accompanying figures and sequences, nevertheless, without being limited thereto. For the purposes of the present invention, all references as cited herein are incorporated by reference in their entireties. In the Figures:

FIG. 1: RIG-I stimulation triggers the release of extracellular vesicles (EVs). (A) Melanoma cells D04mel28 or Ma-Mel-86c29 were analyzed for mRNA expression of RIG-I by quantitative real-time PCR in the presence or absence of type I Interferon (IFN) stimulation. Data are normalized to b-Actin. (n D 3) (B) Functionality of RIG-I signaling in D04mel and Ma-Mel-86c was determined by CXCL10 production 24 h after lipofection of cells with 1 mg/mL ctrl RNA or 3pRNA (n D 3) (C) Schematic overview of experimental procedures. Tumor cells (D04mel or Ma-Mel-86c) were transfected with 3pRNA (RIG-I ligand) or inert control RNA (non-RIG-I ligand) and EVs (RIG-I-EVs vs. ctrl-EVs) were purified using serial ultracentrifugation. Afterwards, EVs were analyzed regarding their effects on immune cells. (D) NTA analysis of purified vesicles (RIG-I-EVs vs. ctrl-EVs) derived from melanoma cells. (E) Cryo electron microscopy shows typical particles obtained by purification. One white or black scale bar indicates 100 nm. (F) Purified vesicles (RIG-I-EVs or ctrl-EVs) derived from D04mel cells were analyzed for expression of CD9, CD63, CD81 by western blot. (G) Purified vesicles (RIG-I-EVs vs. ctrl-EVs) derived from melanoma cells (D04mel, Ma-Mel-86c) were analyzed for CD9 expression by flow cytometry (filled gray: isotype, dashed: ctrl-EVs, black line: RIG-I-EVs). (H) Amount of EVs after stimulation with 3pRNA (RIG-I-EVs) or ctrl RNA (ctrl-EVs) derived from melanoma cells (D04mel, Ma-Mel-86c) were estimated by quantification of proteins using Bradford Assay (n D 4-9). (I) Particle number of EVs after stimulation with 3pRNA (RIG-I EVs) or ctrl RNA (ctrl EVs) derived from melanoma cells (D04mel) was determined by NTA analysis (n D 6). All error bars reflect mean±s.d. *indicates $p<0.05$.

Figure 2:
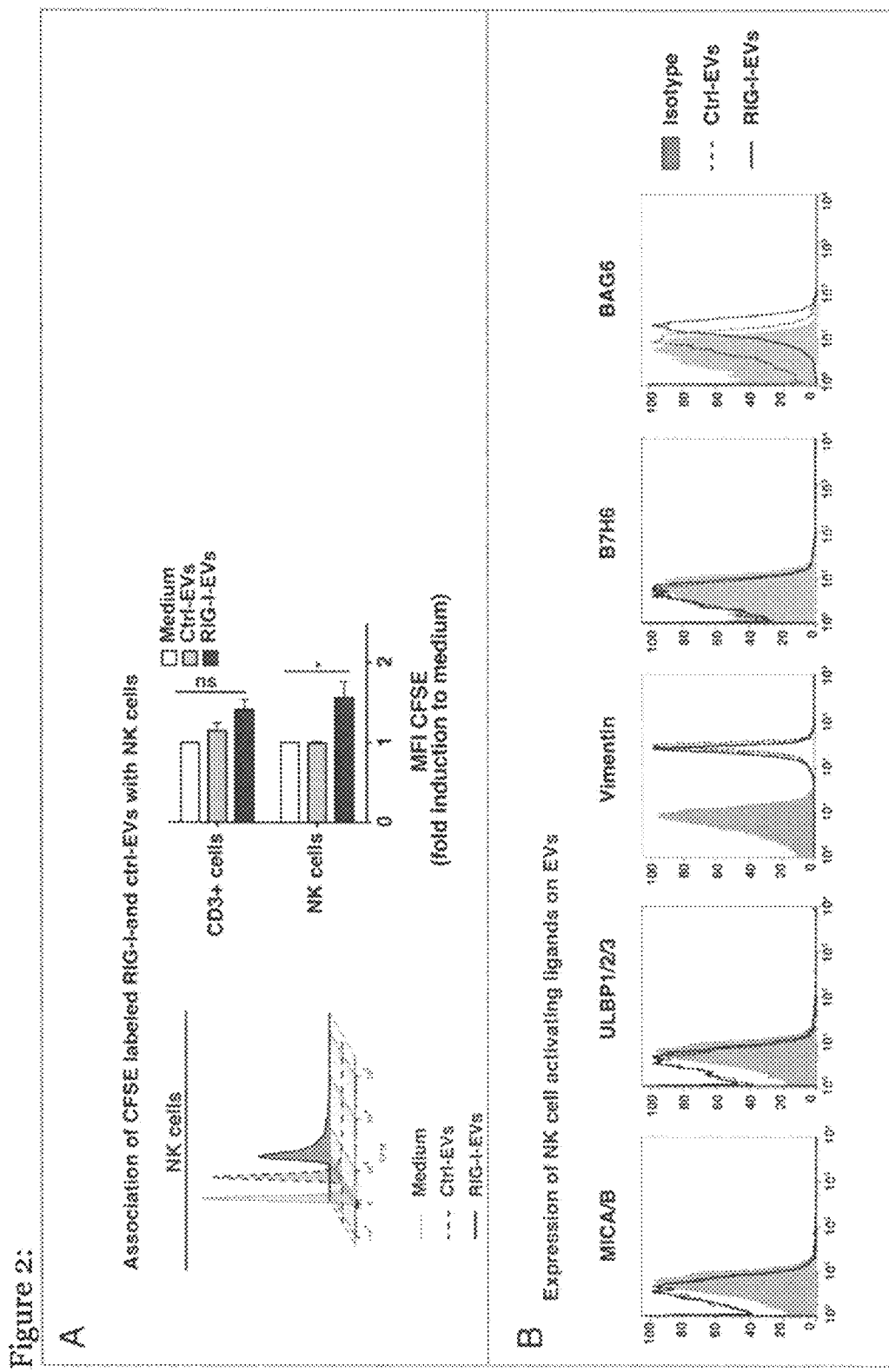
Figure 2:
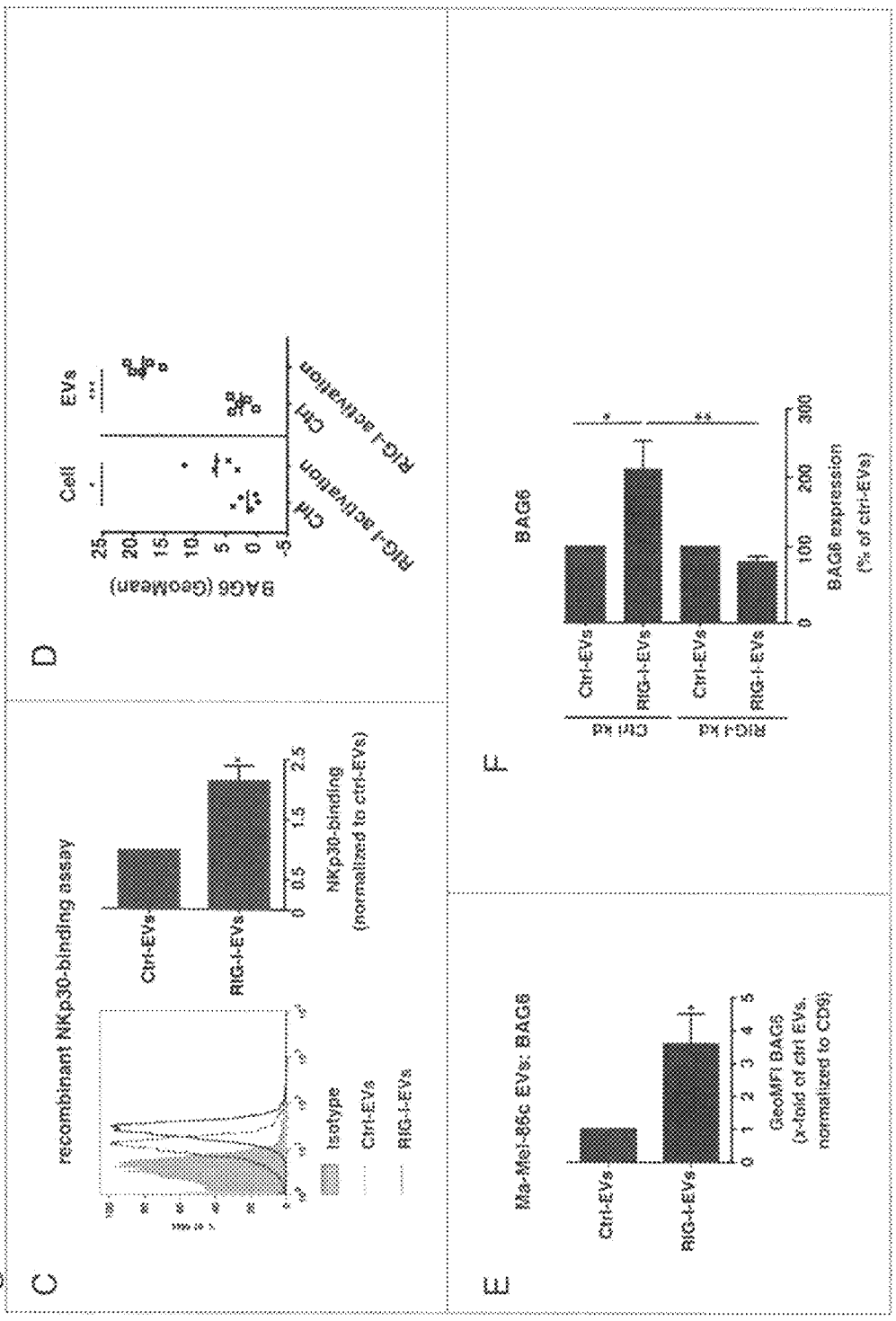

FIG. 2: Evs derived from RIG-I stimulated cells express enhanced levels of the NKp30-ligand BAG6. (A) CFSE labeled EVs (EV protein amount: 10 mg/mL) induced by 3pRNA (RIG-I-EVs) versus ctrl RNA (ctrl-EVs) were incubated with PBMCs and 24 h later CFSE staining of NK cells (CD3 negative, CD56 positive) or CD3 positive lymphocytes (CD3C cells) were determined by flow cytometry (n D 3). (B) D04mel cells were transfected with 3pRNA (RIG-I-EVs) or ctrl RNA (ctrl-EVs) and the expression of MIC A/B, ULBP 1/2/3, Vimentin, B7-H6 and BAG6 on EVs was analyzed by flow cytometry (filled gray: isotype, dashed: ctrl-EVs, black line: RIG-I-EVs). One representative of four independent experiments is shown. (C) EVs induced by 3pRNA (RIG-I-EVs) vs. ctrl RNA (ctrl-EVs) were analyzed for binding of NKp30-fc by flow cytometry. Histogram shows one representative experiment (left, filled gray: isotype, dashed: ctrl-EVs, black line: RIG-I-EVs) and graph (right) shows quantification of x-fold induction of the geometric mean normalized to CD9 (n D 4). (D) Expression level of BAG6 on D04mel cells (left) or D04mel derived EVs (right) after transfection with 3pRNA or ctrl RNA was deter-mined by flow cytometry (n D 5). (E) Purified EVs from melanoma (Ma-Mel-86c) cells induced by 3pRNA (RIG-I-EVs) versus ctrl RNA (ctrl-EVs) were analyzed for BAG6 expression on the surface by flow cytometry. Graphs show % induction of the geometric mean normalized to CD9 and s.e.m. of at least four independent experiments. (F) Exosomes from cells with siRNA mediated control knock down (ctrl kd) or RIG-I knock down (RIG-I kd) were analyzed for BAG6 expression on the surface by flow cytometry in response to 3pRNA (RIG-I-EVs) vs. ctrl RNA (ctrl-EVs). Graph shows geometric mean of BAG6 relative to CD9 (n D 4). All error bars reflect mean±s.d. *,  and * indicates $p<0.05$, $p<0.01$ and $p<0.001$.

Figure 3:
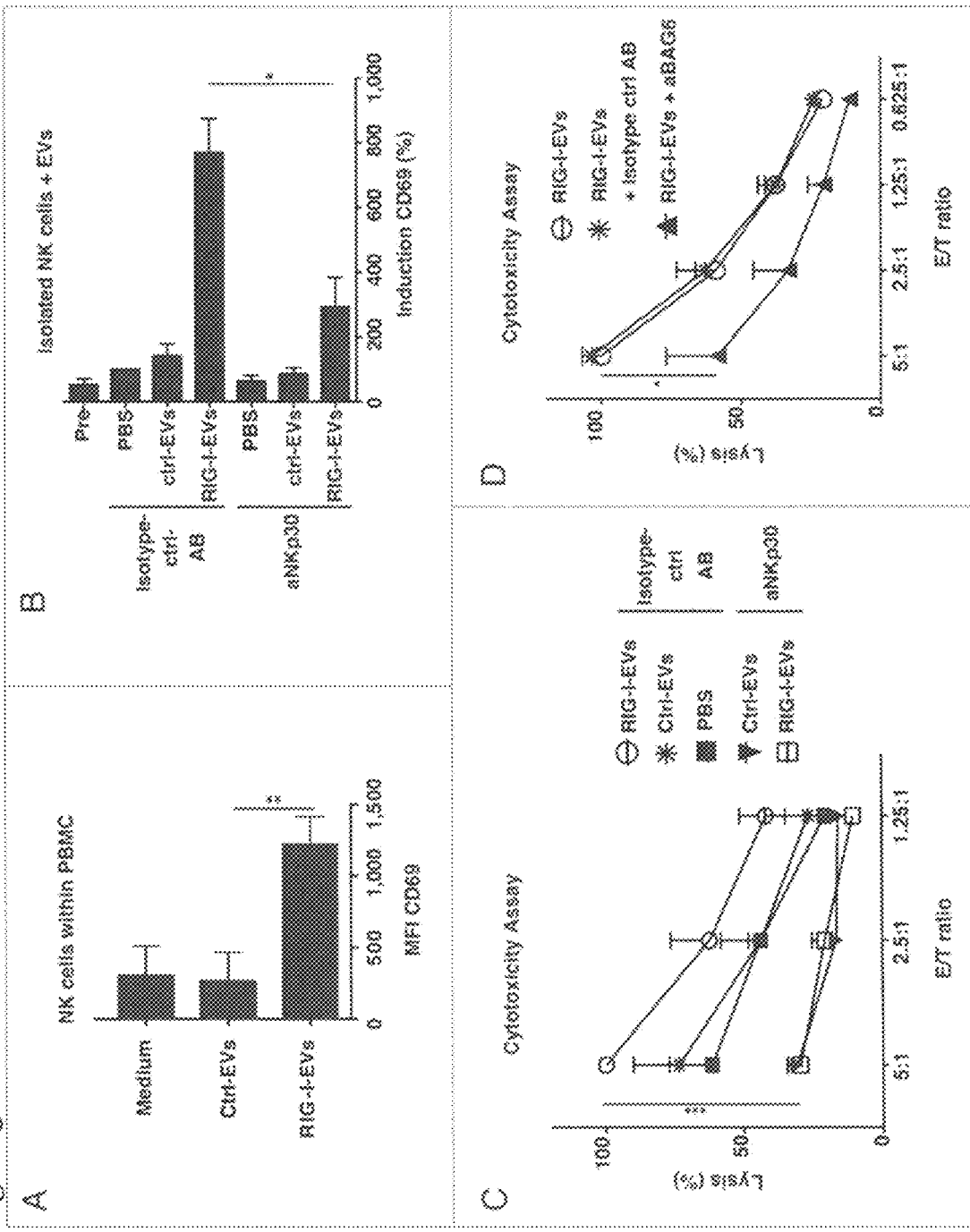

FIG. 3: BAG6-positive RIG-I-EVs induce enhanced NK cell cytotoxicity in vitro. (A) PBMCs were incubated over night with RIG-I-EVs versus ctrl-EVs (EV protein amount: 10 mg/mL) and CD69 expression on NK cells (CD3 negative, CD56 positive) was determined by flow cytometry (n D 3). (B) Primary purified NK cells were left untreated (PBS) or incubated with 100 mg/mL (protein amount) RIG-I-EVs vs. ctrl-EVs for 36 h with (aNKp30) or without blocking (Isotype control antibody (AB)) of NKp30 (clone P30-15). Expression of CD69 (MFI) on NK cells after incubation with EVs was measured and normalized to PBS (n D 3). (CCD) Done as described in (B). (C) Cytotoxicity against untreated melanoma cells (D04mel) was assessed by europium release assay and results were normalized to 100% lysis by RIG-I-EVs in different E/T (n D 3). (D) Instead of NKp30 on NK cells, BAG6 was blocked on EVs with anti-BAG6 (aBAG6). Results were normalized to 100% lysis by RIG-I-EVs in an E/T-ratio of 5:1 (n D 3 for ctrland RIG-I-EVs C aBAG6, n D 2 for RIG-I-EVs C Isotype ctrl antibody). All error bars reflect mean±s.d. *,  and * indicates $p<0.05$, $p<0.01$ and $p<0.001$.

Figure 4:
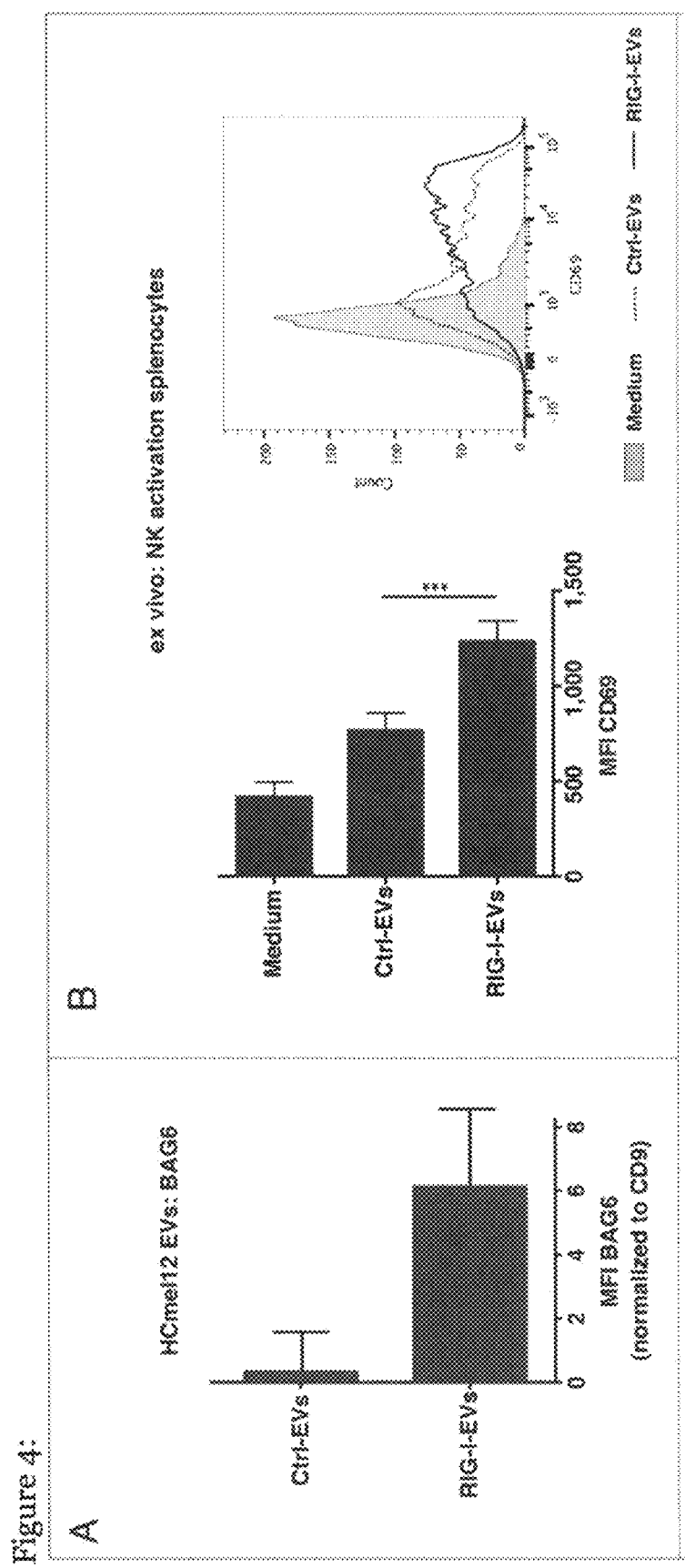
Figure 4:
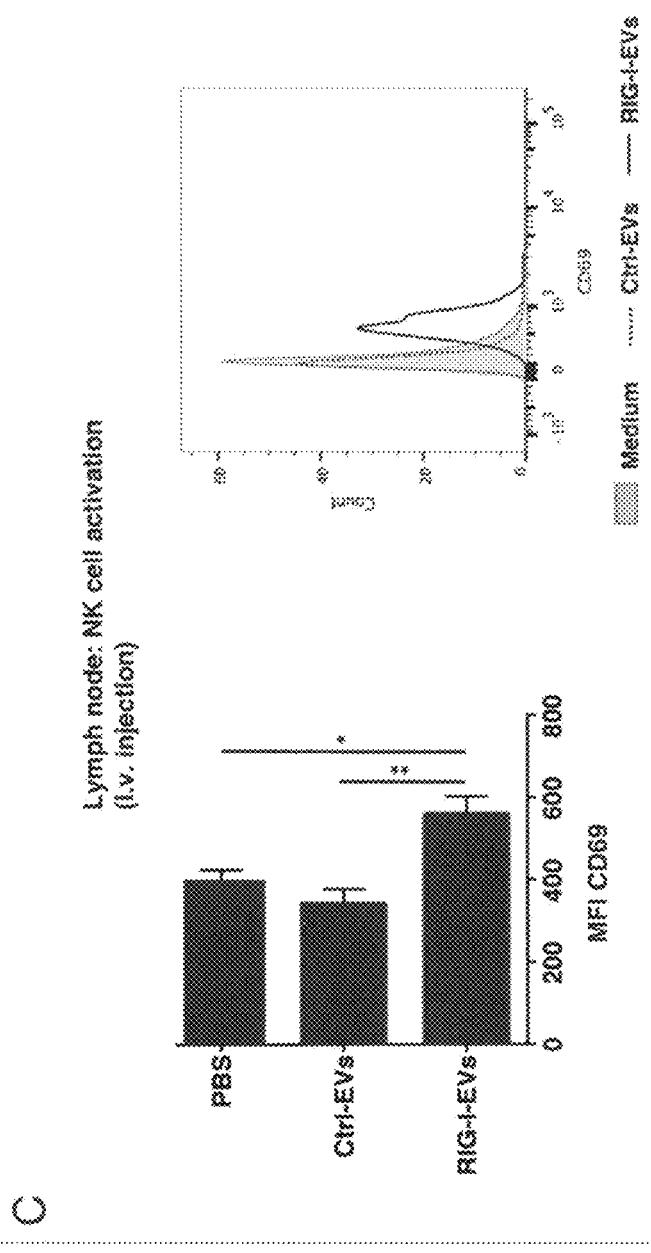
Figure 4:
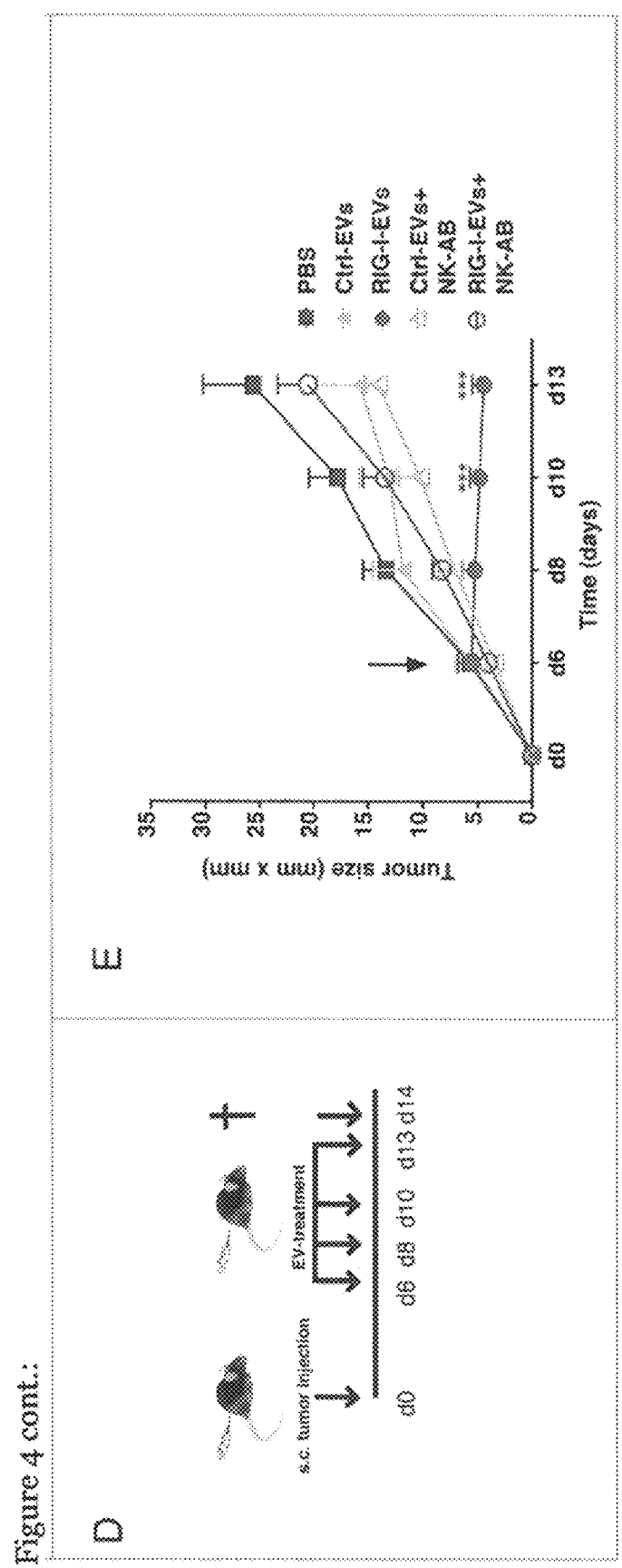

FIG. 4: RIG-I-EVs lead to activation of NK cells and inhibition of tumor growth in vivo. HCmel12 cells were transfected with 3pRNA (RIG-I-EVs) or ctrl RNA (ctrl-EVs) and the expression of BAG6 on EVs was analyzed by flow cytometry (n D 3). (B) Activation of mouse splenocytes with 10 mg/mL (protein amount) EVs ex vivo. Graph (left) shows CD69 expression on NK cells (NK1.1CC$^{D3^j}$) was determined by flow cytometry (n D 5). Right histogram shows one representative experiment (left, filled gray: isotype, dashed: ctrl-EVs, black line: RIG-I-EVs) (C-E) Application of RIG-I- or ctrl-EVs in vivo. (C) HCmel12 mouse melanoma cell derived EVs (20 mg EV protein amount per mouse) were injected intravenously. Graph (left) shows expression of CD69 on NK cells (NK1.1CC$^{D3^j}$) purified from the lymph node was determined by flow cytometry (n D 5). Histogram (right) shows one representative experiment (left, filled gray: isotype, dashed: ctrl-EVs, black line: RIG-I-EVs) (D) Treatment schema of in vivo experiment. C57BL/6 mice were injected with HCmel12 mouse melanoma cells subcutaneously in the flank at day 0 and treated with melanoma-derived EVs at day 6, 8, 10, 13. Melanoma bearing mice were treated with PBS (ctrl), 20 mg protein amount of 3pRNA-induced EVs (RIG-I-EVs) or EVs induced by control RNA (ctrl-EVs), both derived from HCmel12 cells. Mice were sacrificed at day 14. (E) Tumor size was measured in treated and untreated mice with or without depletion of NK cells using antibody directed against NK1.1 (NK-AB). Mean tumor size and s.d. of 5-9 animals are shown. Arrow indicates begin of treatment, filled square: PBS, filled triangle: ctrl-EVs, filled circle: RIG-I-EVs, empty triangle: ctrl-EVsCNK-AB, empty circle: RIG-I-EVsCNK-AB. *,  and * indicates $p<0.05$, $p<0.01$ and $p<0.001$.

Figure 5:
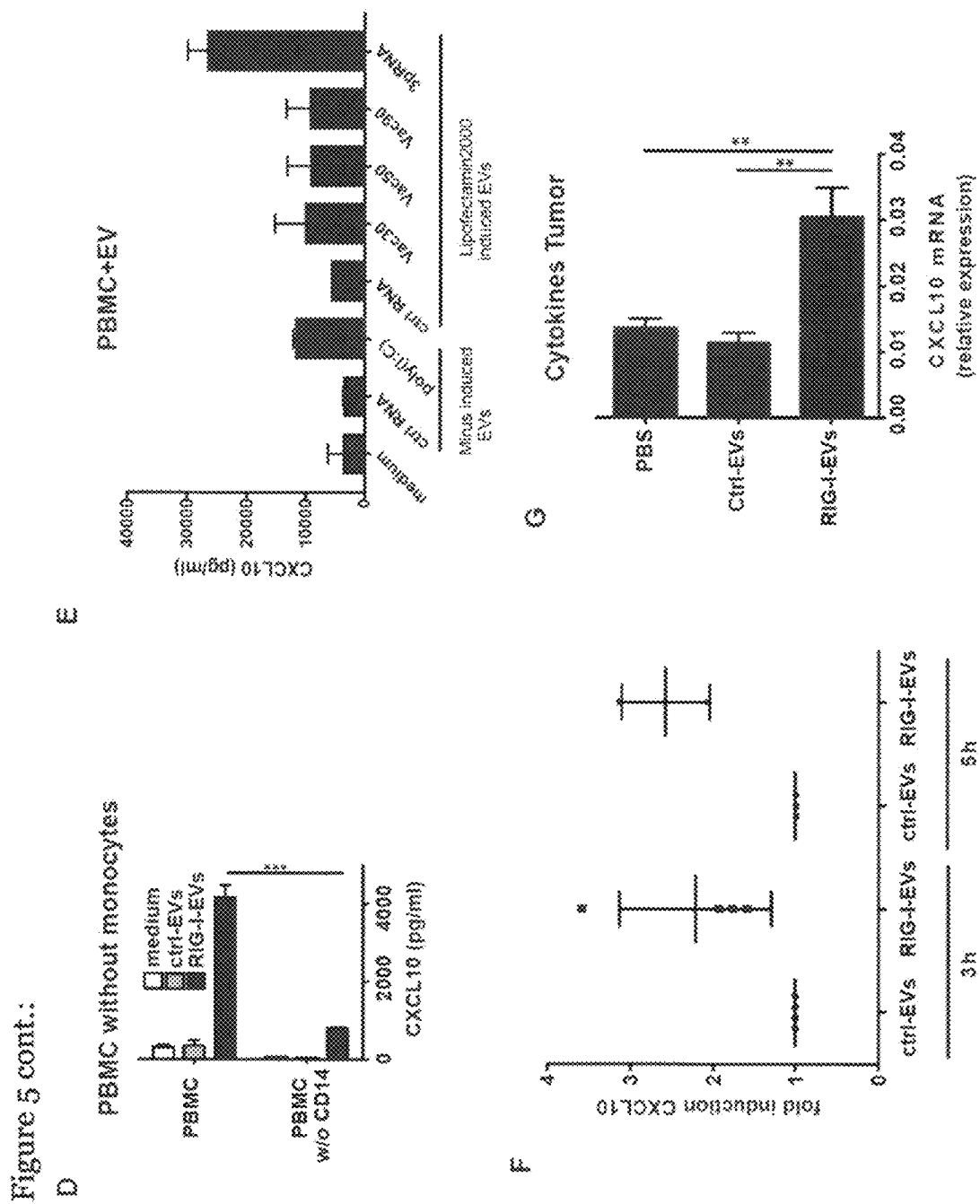

FIG. 5: 3pRNA induced melanoma derived EVs lead to the production of type I IFN. Primary human melanoma cells (D04mel) were transfected with 3pRNA (RIG-I ligand) or inert control RNA (non-RIG-I ligand) and EVs (RIG-I-EVs vs. Ctrl-EVs) were purified. Afterwards EVs were analyzed regarding their effects on immune cells. (A) CFSE labeled EVs (EV protein amount: 10 µg/ml) induced by 3pRNA (RIG-I-EVs) versus ctrl RNA (ctrl-EVs) were incubated with PBMCs and 24 h later CFSE staining of CD14+ monocytes (left: histogram), NK cells (CD3 negative, CD56 positive) and lymphocytes without NK cells (Lymph w/o NK) were determined by flow cytometry (n=3). (B) Activation of monocytes by RIG-I-EVs within PBMCs was measured by expression of CD86 (n=3). (C) 3pRNA (RIG-I_EVs) versus ctrl RNA (ctrl EVs) induced EVs were incubated with PBMCs and cytokine secretion of IL1□, IL6, IL8, IL12(p70), IL15, TNF□, CXCL10 and type I IFN was determined after 24 h (n=3-6). (D) Either PBMCs or PBMCs depleted of CD14+ monocytes (PBMC w/o CD14) were incubated over night with RIG-I-EVs versus ctrl-EVs (EV protein amount 10 µg/ml) and production of CXCL10 was measured (n=4). (E) C57/B16 mice were i.v. injected with 3pRNA or ctrl RNA induced EVs and induction of CXCL10 was determined in the serum (n=4). (F) Melanoma bearing mice were i.t. injected with 3pRNA (RIG-I-EVs) or ctrl RNA induced EVs (ctrl EVs) and mRNA expression of CXCL10 within the tumor was measured by qPCR (G). Data shows relative expression of CXCL10 to β-actin of nine mice.

Figure 6:
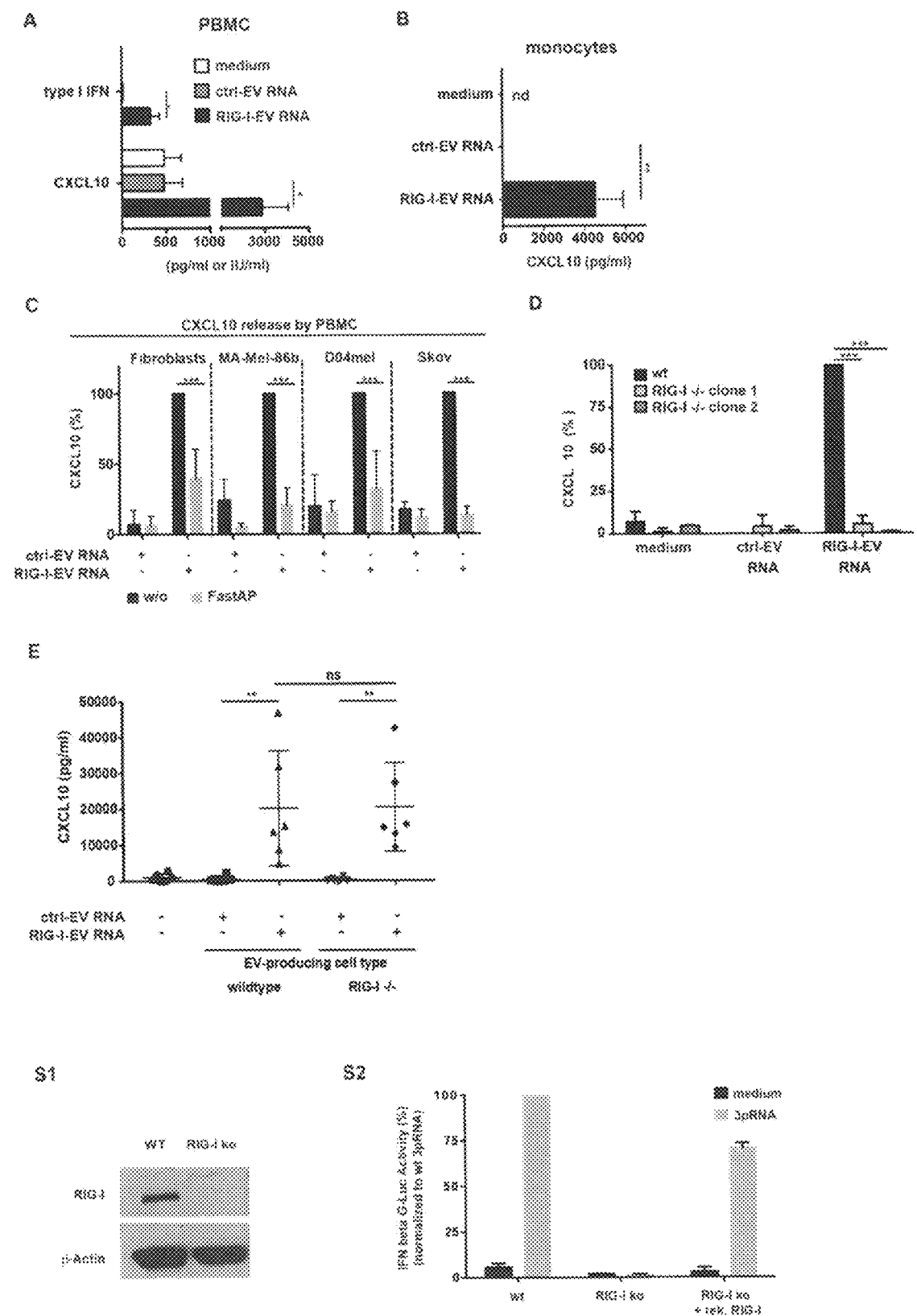

FIG. 6: RIG-I induced melanoma EVs transfer functional RIG-I ligands; (A) PBMCs were stimulated with 50 ng/ml RNA from EVs derived from melanoma cells (D04mel)

induced by 3pRNA (RIG-I-EVs) versus ctrl RNA (ctrl EVs). 24 h later CXCL10 and type I IFN was measured in the supernatant (n=4). (B) Done as described in (A). Isolated CD14+ monocytes were incubated for 24 h with EV-RNA and CXCL10 production was measured in the supernatant (n=3). (C) PBMCs were stimulated with EV-RNA derived from two different melanoma cells lines (D04mel, MA-Mel-86), human primary fibroblasts or ovarian cancer cell line (Skov) with or without (w/o) digestion of 5'-3p moieties using FastAP thermosensitive alkaline phosphatase (FastAP). 24 h later CXCL10 was measured in the supernatant (n=4). (D) RIG-I expressing wt cells or two different CRISPR RIG-I knock out clones (RIG-I−/− clone 1 and clone 2) were stimulated with RNA from EVs (50 ng/ml) induced by 3pRNA (RIG-I-EVs) versus ctrl RNA (ctrl-EVs). 24 h later production of CXCL10 was measured by ELISA (n=3). (E) PBMCs were stimulated with RNA from EVs derived from RIG-I wt or RIG-I knock out cells stimulated with 3pRNA or ctrl RNA. 24 h later CXCL10 was measured in the supernatant (n=6). (S1) RIG-I expression in RIG-I wild type (WT) and knock out cells (RIG-I ko) was determined by western blot. β-Actin is used as loading control. (S2) Measurement of IFN-beta Luciferase activity after stimulation of wildtype (wt) or RIG-I knock out (RIG-I ko) cells with 3pRNA (66 ng/ml) or after reconstitution of RIG-I ko cells with recombinant (rek.) RIG-I protein (60 ng). Data are normalized to IFN-beta Luciferase activity of wt cells stimulated with 3pRNA (n=3). All error bars reflect mean±s.d.

Figure 7:
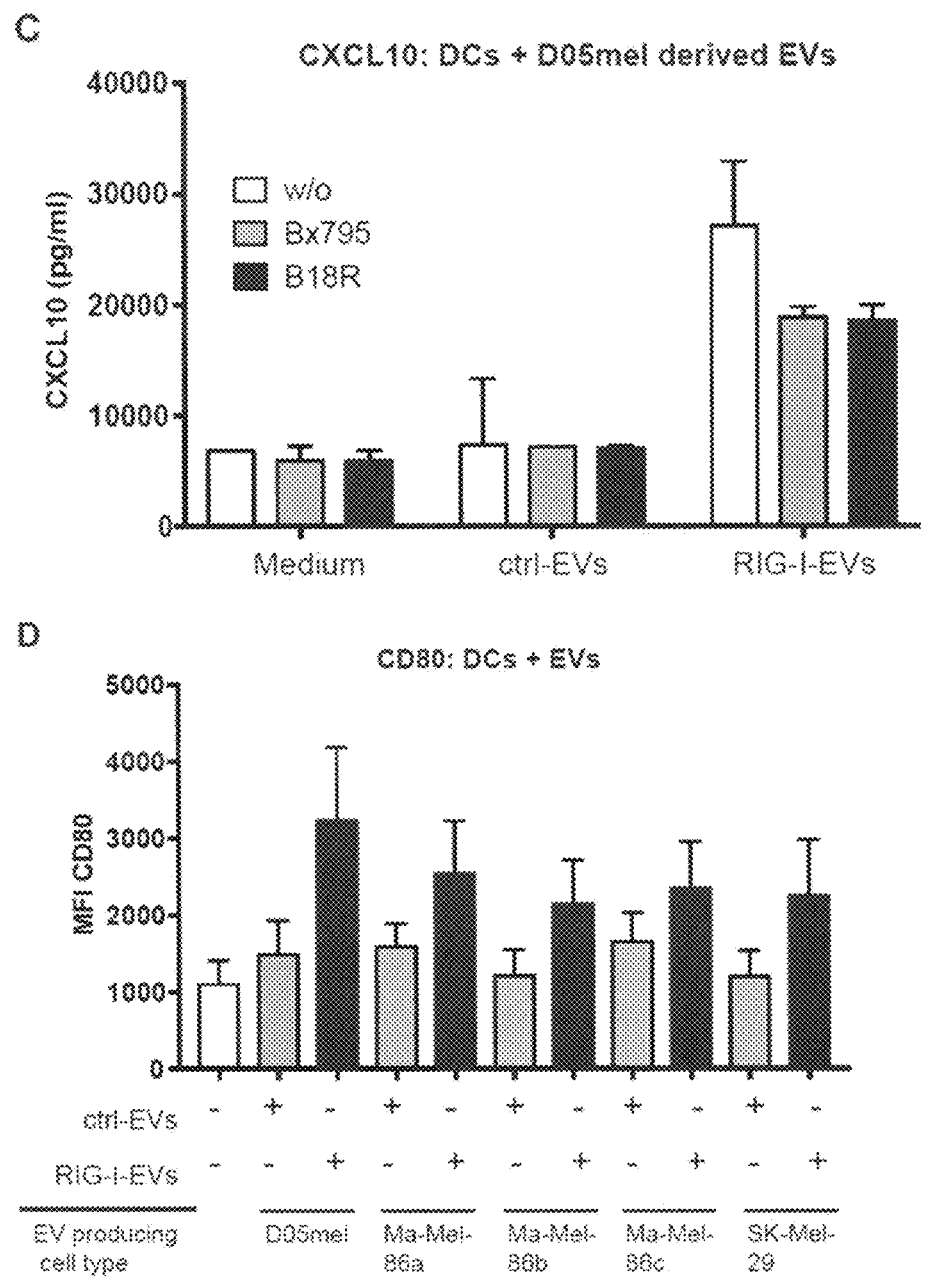
Figure 7:
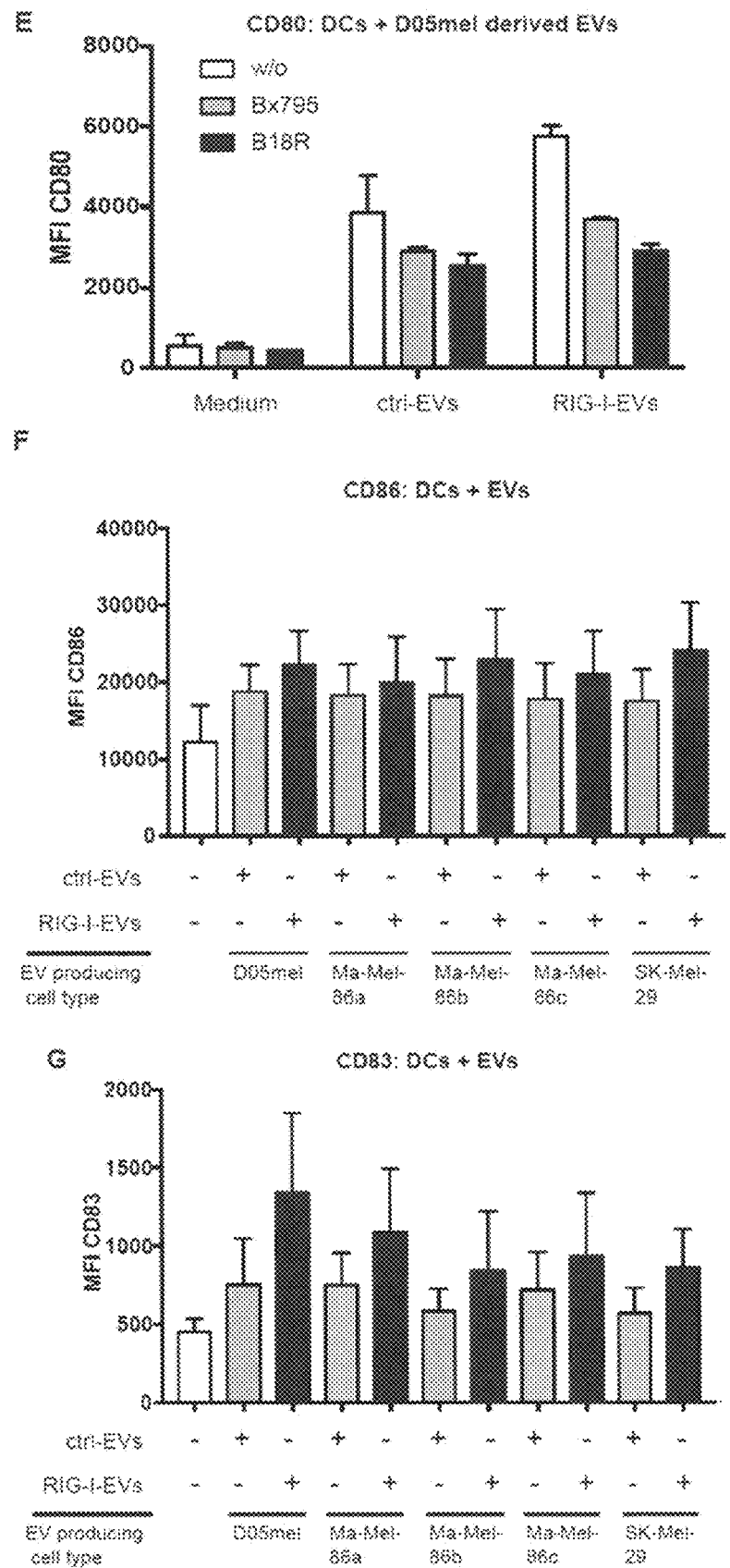

FIG. 7: RIG-I induced EVs induce DC maturation (A) Primary human melanoma cells (Ma-Mel-86a/b/c, D05mel and SK-Mel-29) were transfected with 3pRNA (RIG-I ligand) or inert control RNA (non-RIG-I ligand) and EVs (RIG-I-EVs vs. Ctrl-EVs) were purified. Immature human DCs were incubated with ctrl-EVs or RIG-I-EVs (75 µg/ml) and production of type I IFN was measured in the cell free supernatant (n=3). (B) Done as described in (A) but production of CXCL10 was quantified by ELISA (n=3). (C) D05mel primary melanoma cells were transfected with 3pRNA (RIG-I ligand) or inert control RNA (non-RIG-I ligand) and EVs (RIG-I-EVs vs. Ctrl-EVs, 75 µg/ml)) were purified to stimulate human immature DCs in the presence of Bx795 (TBK1 Inhibitor), B18R (type I IFN binding protein) or in the absence (w/o) of any inhibitors. After 24 h cytokine secretion of CXCL10 was determined by ELISA (n=2). (D-G) Immature human DCs were incubated with EVs (75 µg/ml) derived from primary human melanoma cells (Ma-Mel-86a/b/c, D05mel, SK-Mel-29) transfected with 3pRNA (RIG-I ligand) or inert control RNA (non-RIG-I-ligand). (D) Maturation of human DCs by EVs was detected by expression of CD80 by flow cytometry. (E) D05mel derived EVs (ctrl-EVs vs RIG-I-EVs) were incubated with immature DCs (w/o), in the presence of the TBK1 Inhibitor Bx795 or the type I IFN binding protein (B18R) and expression of CD80 on DCs was measured by flow cytometry (n=2). (F) Done as described in (D). Expression of CD83 on DCs was measured (n=3). (G) Done as described in (D) and expression of CD86 was determined by flow cytometry (n=3).

Figure 8:
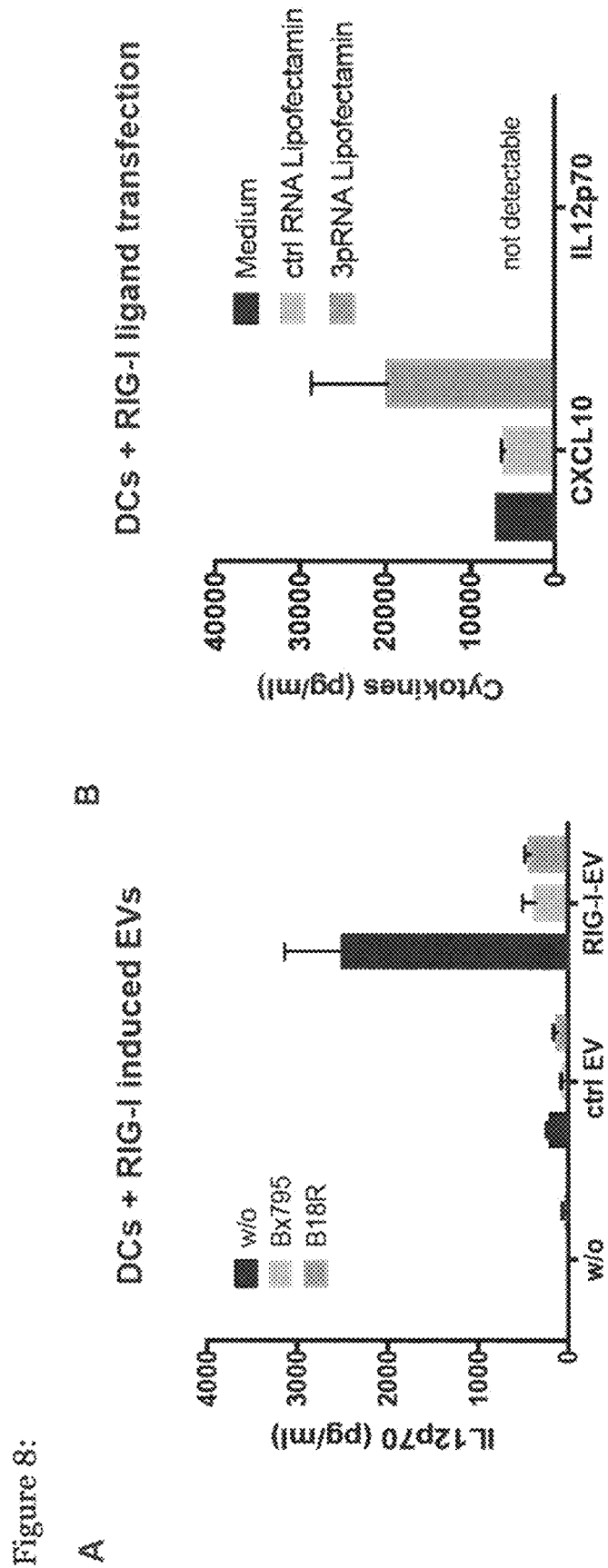
Figure 8:
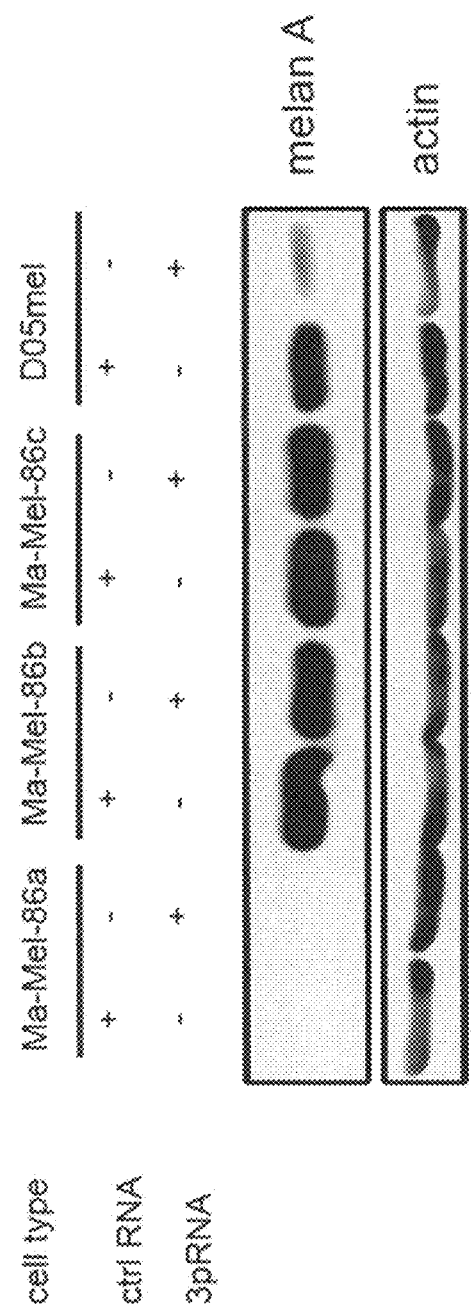
Figure 8:
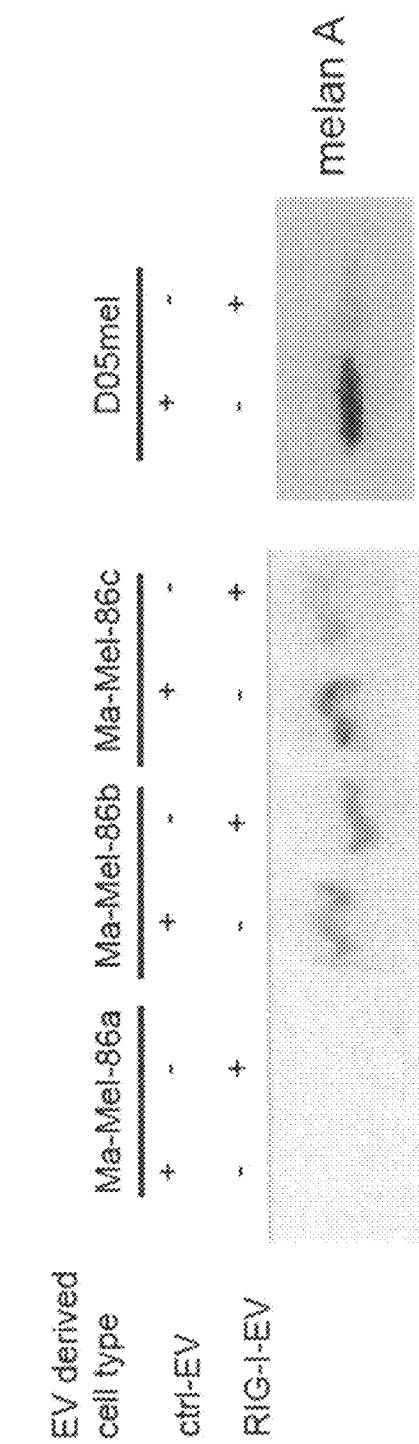

FIG. 8: Transfer of RIG-I ligand and tumor antigen in EVs promote antigen-specific T cell responses (A) Primary human melanoma cells (D05mel) were transfected with 3pRNA (RIG-I ligand) or inert control RNA (non-RIG-I ligand) and EVs (RIG-I-EVs vs. Ctrl-EVs) were purified. Immature human DCs were incubated with ctrl-EVs or RIG-I-EVs (75 µg/ml) and production of IL12p70 in the presence of the TBK1 Inhibitor Bx795 or the type I IFN binding protein (B18R) was measured in the cell free supernatant (n=3). (B) As control experiment, immature human DCs were transfected with 3pRNA (RIG-I ligand) or inert control RNA (non-RIG-I ligand) with lipofectamin2000 (transfection reagent) and production of CXCL10 and IL12p70 was measured in the supernatant (n=3). (C) Ma-Mel-86a, Ma-Mel-86b, Ma-Mel-86c and D05mel were transfected with 3pRNA (RIG-I ligand) or inert control RNA (non-RIG-I ligand) and expression of melan A was detected by western blot. Actin is used as loading control. One representative blot is shown. (D) Done as described in (C) but EVs were isolated from indicated cell lines. Equal amount of cells was used for EV production and expression of melan A was detected by western blot. (E) Antigen-specific T cell response induced by RIG-I-EVs was determined by human IFNg ELISPOT Assay. HLA-A2 positive DCs were incubated with ctrl-EVs or RIG-I-EVs (75 µg/ml, derived from D05mel) and melan A (upper panel) or tyrosinase (bottom panel) sensitive autologous T cell clones were added and production of IFNg was monitored. Assay performance was controlled while using only T cells, DCs with no loading of EVs in the presence of T cells (DCs+T cells) and incubation of T cells with D05mel melanoma cells (T cells+Melanoma cells) as positive control.

EXAMPLES

Materials and Methods

Antibodies and Reagents

Fluorophore conjugated antibodies against human CD3, CD9, CD56, CD80, CD83, CD86 and CD69 and murine CD3, NK1.1 and CD69 were obtained from BD or BioLegend. For staining of EVs anti-human MICA/B. ULBP1, ULBP2, ULBP3, CD9 and as secondary antibody goat-a-mouse-PE, monoclonal mouse-a-human-BAG6 (Pogge, unpublished, clone 3E4) were used. Binding of recombinant NKp30fc protein was detected by Cy3 anti-human fc from Dianova. For blocking experiments, a human NKp30, monoclonal mouse-a-human BAG6 and IgG1-isotype control were used. Recombinant human IFNa2a was purchased from Miltenyi. IFN-gamma antibody set for ELISPOT Assay was obtained from Mabtec. Cytokine data (IL1b, IL6, IL8, IL12p70, CXCL10 and TNFa) were obtained while using ELISA Sets from BD or eBioscience (IL15, IFNa). HEK-Blue cells from Invivogen were used for quantification of Type I IFN in the cell free supernatant of cells. Melan A antibody was purchased from Abcam.

Immunostimulatory Oligonucleotides

For generation of DNA-template-dependent in vitro-transcribed RNA (3pRNA), the oligonucleotide 1 (reverse) (50-GGGAC GCTGACCCAGAAGATCTACTAT-TTCTAGTAGATCTTCT GGGTCAGCGTCCCTATAGT-GAGTCGTATTACAA-30 [SEQ ID NO: 1]) was hybridized with oligonucleotide 2 (forward) (50-TTGTAATAC GACT-CACTATAGGGACGCTGACCCAGAAGATCTACTAG AAATAGTAGATCTTCTGGGTCAGCGTCCC-30 [SEQ ID NO: 2], obtained from Biomers) in hybridization buffer (250 mM Tris-HCl, 250 mM NaCl, pH 7.4) for 5 min at 90° C. The hybridized product is directly used as a template for in vitro transcription reaction with a commercial in vitro T7 high-yield transcription kit according to the manufactures protocol. Afterwards, the transcription product is digested with DNase I and purified with Mini Quick spin columns from Roche. As negative control (ctrl RNA), a poly-A RNA obtained from Sigma was used. Poly(I:C) was obtained from Invivogen. Vac30, Vac50 and Vac90 were obtained from Metabion with the following sequences for Vac30: GGGAT-GAGTAAAGGAGAAGAACTTTTAGGG[SEQ ID NO: 3] and GGGTAAAAGTTCTTCTCCTTTACTCATGGG[SEQ ID NO: 4]; Vac50: GGGAT-GAGTAAAGGAGAAGAACTTTTCACTGGAGT-TATCCCAGTTATGGG[SEQ ID NO: 5] and GGGA-TAACTGGGATAACTCCAGTGAAAAGTTCTTCTCCTT-TACTCATGG[SEQ ID NO: 6]; Vac90: GGGATGAGTAAAGGAGAAGAACTTTTCACTG-GAGTTATCCCAGTTATTGTTGAATTAGATGGC GATGTTAATGGGCAAAAATTCTCTGGG[SEQ ID NO: 7] and GGGAGAGAATTTTTGCCCATTAACATCGC-CATCTAATTCAACAATAACTGGGATAACTCCAGTG AAAAGTTCTTCTCCTTTACTCATGGG [SEQ ID NO: 8]

Cell Culture

The human melanoma cell line D04mel is available through the Australasian Biospecimen Network (Oncology) Cell Line Bank at the QIMR Berghofer Medical Research Institute and was a kind gift of C. W. Schmidt. The human melanoma cell line Ma-Mel-86a, Ma-Mel-86b, Ma-Mel-86c was provided by A. Paschen. The mouse melanoma cell line (HCmel12) was derived from a primary melanoma in HGF/SF-CDK4(R24C) mice by serial transplantation.33 Cells were cultured in RPMI with penicillin (1%) and streptomycin (1%) and 10% FCS (Gibco). HEK Blue cells (Invivo-Gen) were maintained in DMEM containing 10% FCS and Pyruvate (1%). Skov cells were obtained from ATCC. In case of EV isolation experiments cells were cultured with vesicle-reduced FCS. For culture of PBMCs, freshly prepared buffy coats from human healthy donors were obtained from the blood bank with the donors' written informed consent after approval by the responsible ethic committee. PBMCs were prepared by density gradient centrifugation using Biocoll (Biochrom). Isolation of NK cells or CD14+ monocytes from PBMCs was performed by MACS using NK-Isolation Kit or CD14-Microbeads (Miltenyi) according to the manufacturer's instruction. Purity of isolated NK cells or monocytes was determined by FACS-Analysis to be 95%.

Isolation of Splenocytes

Splenocytes were isolated from C57BL/6 mice. Spleens were mashed through a cell strainer and red blood cells were lysed. Per 96 well 400,000 splenocytes were used and incubated with 10 mg/mL EVs for 24 h followed by flow cytometric staining Generation of RIG-I Knockdown Cells For knockdown of RIG-I D04mel, cells were transfected with 20 pmol RIG-I siRNA or control siRNA (SantaCruz, USA, Tex., Dallas) with lipofection 24 h and 5 h prior transfection with RIG-I ligand or control RNA.

Generation of CRISPR Knock Out Cells

A549 cells were transfected with Lipofectamine 2000 (Life technologies) with 200 ng of a CAS9-gRNA expression plasmid targeting RIG-I (GGGTCTTCCGGA-TATAATCC(TGG)[SEQ ID NO: 9]). 48 h after transfection cells were grown at limiting dilution conditions in 96 well plates (0.7 cells per well). After 14 days growing clones were selected and screened for knockout by functional testing, western blot and/or Sanger sequencing.

Transfection of Tumor Cells

Melanoma cells were grown in 10 cm dishes and at a confluence of 70-80% (5£106 cells) cells were transfected with 3pRNA, poly(I:C), Vac30, Vac50 or Vac90 or poly-A RNA (ctrl RNA) as control. Therefor, 24 mg RNA were complexed with 60 mL Lipofectamin2000 or Mirus according to the manual and cells were incubated for 3 h with the transfection complexes. Afterwards, cells were washed three times to remove lipofection complexes and cells were further cultured for 18 h in media supplemented with EV-reduced FCS for pro-duction of EVs.

Stimulation of Cells with 3pRNA and Exosomal-RNA

If not indicated differently, 1 µg/ml 3pRNA (RIG-I ligand), non-stimulatory CA20-RNA (control RNA or ctrl) or RNA purified from exosomes was transfected with Lipofectamine2000® (Invitrogen, Karlsruhe, Germany) according to the manual. After 3 h of stimulation, Lipofectamine2000® bound 3pRNA was removed by washing cells three times with PBS. If indicated, 40 µg exosomal RNA was digested with 1 U FastAP thermosensitive Alkaline Phosphatase (Fermentas, St. Leon Roth, Germany).

Extracellular Vesicle (EV) Purification and Labeling

Human melanoma cells (D04mel, Ma-Mel-86c) or mouse melanoma cells (HCmel12) were cultured in media with EVreduced FCS (100,000 g for 90 min). Supernatant of cells for EV purification was centrifugated for 5 min at 400 g and twice for 15 min at 10,000 g. Vesicles were pelleted twice at 100,000 g for 90 min with intermediate resuspension in PBS (SW32Ti Rotor, Beckman Coulter). The amount of EV protein (approximately 20-100 mg from 5£106 cells, dependent whether cells were activated with RIG-I ligand or not) was quantified by Bradford Assay (Carl Roth) or via Nanodrop (Peqlab, Erlangen, Germany) and equal amounts of EV protein were used in experiments (dependent on experiment between 10-100 mg/mL). To label EVs, melanoma cells were incubated with 5 mM carboxyfluorescein succinimidyl ester (CFSE) (eBioscience).

Nanoparticle Tracking Analysis

EVs were analyzed with NTA using the Nanosight NS300 (Malvern Instruments Ltd., Worcestershire, UK).

Stimulation of Immune Cells with Extracellular Vesicles (EVs)

NK cells or PBMCs were incubated with different amounts of EVs quantified by Bradford Assay or Nanodrop with incubation times between 24 h (for PBMC studies: 10 mg/mL EV amount) to 48 h (NK activation and cytotoxicity experiments: 100 mg/mL EV amount).

Isolation of RNA

RNA was purified from exosomes using miCURY RNA Isolation Kit-Cell & Plant from Exiqon (Vedbaek, Denmark) as described in the manual. Amount of isolated RNA was determined by Nanodrop (Erlangen, Germany). RNA isolation from tumor tissue was done by using RNeasy FFPE Kit (Quiagen, Hilden, Germany) as recommended in the manual Quantitative Real-Time PCR cDNA Synthesis was performed using VILO cDNA Synthesis Kit from Life Technologies (#11754050) as described in the manual. For human, RIG-I cDNA was amplified in a total vol-ume of 20 mL using LightCycler 480-System (Roche, Germany, Mannheim). Primer- and Probe-designs were performed using Universal Probe Library (Roche, Germany, Mannheim). Used Probes from Roche were #63 for murine b-actin, #18 for murine CXCL10. Following PCR conditions were used: 95° C. for 10 min, followed by 50 cycles of 95° C. for 10 s, 60° C. for 30 s and 72° C. for 1 min.

Flow Cytometric Analysis

For flow cytometric analysis, EVs were bound to carboxylated polysterene microbeads (4.5 mM, Polyscience Inc.) and stained with antibodies. In addition, the expression of the tetraspanin CD9 was used for quantitation of EVs bound to the beads. Cells and EVs were measured using BD LSRII or FACS Calibur (Heidelberg, Germany) and analyzed using FlowJo (Tree Star, Olten, Switzerland) software. Activation of purified NK cells after 36 h incubation with 100 mg/mL EVs was analyzed by flow cytometry. NK cells were stained with CD69 and measured using FACS Calibur (Heidelberg, Germany).

Western Blot

EVs or cells were either lysed (2 mM MgCl2, 50 mM Tris HCl pH 7.4, 150 mM NaCl, 1 mM DTT, 1% CHAPES, 1£ Protease-Inhibitor) or loaded directly onto the gel. Equal amounts of total protein were separated by SDS gel electrophoresis and transferred onto a nitrocellulose membrane (GE Healthcare, Freiburg, Germany). For CD9, CD63, CD81 (all 1:200) detection membranes were incubated with the respective antibodies at 4° C. overnight. HRP coupled secondary antibodies a-rat (1:5,000) or a-mouse (1:10,000) (both Jackson ImmunoResearch,) were incubated for 1 h at RT. Membranes were exposed to x-ray films after treatment with ECL western blotting substrate (Thermo Scientific, St. Leon-Rot, Germany).

Cytotoxicity Assay

NK cell-mediated cytotoxicity was analyzed by a standard 3 h europium release assay in a 96-well microtiter plate as previously described (Strandmann et al. 2006). Briefly, NK effector cells were mixed with europium chloride (Sigma) labeled 5£103 target cells (D04mel) at different ratios. Supernatant was assayed for europium release after 3 h in a Wallac Victor 1420 multi-label counter. The percentage of specific lysis was calculated as 100×[(experimental release–spontaneous release)/(maximal release–spontaneous release)]. NK cells were treated in the following way: Blocking of NKp30 was performed by pre-incubation of NK cells with 10 mg/mL of the blocking antibody clone P30-15 (BioLegend) or equivalent amount of an isotype control (ms IgG1, BioLegend) before addition of EVs (100 mg/mL) or PBS control. EVs were purified from 3pRNA or control RNA transfected D04mel cells. For BAG6-blocking experiments, EVs were pre-incubated with 10 mg/mL a-BAG6 antibody (clone 3E4) or corresponding isotype antibody for 30 min on ice. To prevent unspecific NK cell activation via CD16, NK cells were pre-incubated with 10 mg/mL human IgG antibody before addition of BAG6 or isotype ctrl pre-incubated EVs. NK cells were incubated for 40 h with EVs prior performance of the cytotoxicity assay.

DC-T-Cell Co-Culture Assay

DCs were generated from HLA-A2 positive healthy PBMC donors while using adherence method and GMCSF and IL4 (both obtained from Immunotools) overnight followed by DC-loading with EVs (75 µg/ml) for 24 h. T cell clones reactive for MelanA and Tyrosinase were used as IFNg producing cell type in an autologouse reaction. Therefore, EV-loaded DCs were co-cultured with T cells and production of IFNg was determined by ELISPOT Assay.

Cryo Electron Microscopy

The vesicle pellet was suspended in 50 mL PBS. Approximately 3 mL were applied on a 400£100 mesh Quantifoil S7/2 holey carbon film on Cu grids (Quantifoil Micro Tools GmbH, Jena, Germany). After removal of excessive liquid, the grids were immediately shock-frozen by injection into liquid ethane. The grids were transferred into the transmission electron microscope (Leo 912Ω-mega, Leo, Oberkochen, Germany) and analyzed under the atmosphere of liquid nitrogen (−183° C.). The instrument was operated at 120 kV and pictures with a 6,300 to 12,500-fold magnification were taken.

In Vivo Experiments

Animal studies were approved by the local regulatory agency (Landesamt fur Natur, Umwelt and Verbraucherschutz, NRW, Germany). For isolation of serum derived exosomes 12 weeks old C57BL/6 mice were injected intravenously with 50 µg 3pRNA or ctrl RNA delivered with in vivo jetPEI® (Polyplus, Illkirch, France) in a N/P ratio of 8. 3 h and 5 h after injection serum was collected and exosomes respective RNA derived from serum exosomes was isolated as described above. For tumor-treatment experiments: 12 weeks old C57BL/6 mice were injected subcutaneously in the flank with 1.5£105 HCmel12 mouse melanoma cells. Treatment of mice was started at day 6 when all tumors were at least 2£2 mmin size. Tumor size (D length £ width) was measured at days 6, 8, 10 and 13. HCmel12 cells were treated with 3pRNA (see above) or negative control RNA and EVs were purified from supernatant. EVs (20 mg EV protein per mouse) were injected into the tumor in 50 mL of PBS at day 6, 8, 10 and 13. Blood was taken 6 h before sacrificing mice at day 14. Mice were sacrificed when tumors reached 10 mm £10 mm or tumor treatment day 14. NK cell depletion in mice was done using 100 mg NK1.1 antibody per mice (Bio X Cell, #BE-0036) by i.p. injection at day 4, 6, 8 and 13. To analyze NK cell activation within lymph nodes, HCmel12 derived EVs (20 mg EV protein per mouse) were injected intravenously. Lymph nodes were harvested after 18 h and CD69 expression on NK cells was measured.

Statistics

Graphs show mean and standard deviation if not stated differently. Statistical analysis was performed using non-parametric two-sided paired t-test. In case of multiple comparison, one way or two way ANOVA was used followed by Tukey test or Bonferroni to correct for multiple testing. * indicates $p<0.05$,  $p<0.01$ and * $p<0.001$.

Example 1: RIG-Stimulation Triggers the Release of Extracellular Vesicles (EVs)

To analyze the effect of RIG-stimulation on formation and function of tumor-EVs, the inventors used the human melanoma cell lines D04mel and Ma-Mel-86c.28,29 In line with RIG-as type Interferon (IFN)-dependent gene, baseline expression of RIG-in all used cell lines was strongly increased by type IFN (FIG. 1A). In response to activation of RIG-with its ligand 3pRNA, D04mel and Ma-Mel-86c produced the IFN-dependent chemokine CXCL10 (FIG. 1B), demonstrating functional expression of RIG-I.

The experimental setting how EVs were analyzed is depicted in FIG. 1C: Cells were transfected with the RIG-ligand 3pRNA or an inert RNA (non-RIG-I-targeting) as control. Subsequently, the EV fractions were purified from cell culture supernatant as previously described and referred to as RIG-I-extracellular vesicles (RIG-I-EVs) or control RNA extracellular vesicles (ctrl-EVs).11 Analysis of purified vesicles by nanoparticle tracking (NTA) as well as electron microscopy revealed vesicles around 100-140 nm with cup-shaped structure (FIGS. 1D, E), as has been described for exosomes.30,31 Western Blot (FIG. 1F) and flow cytometry (FIG. 1G) confirmed the expression of the exosomal markers CD9, CD63 and CD81. Stimulation of melanoma cells with 3pRNA increased the protein concentration in the EV fraction (FIG. 1H) in line with increased numbers of released EVs (FIG. 1I) in comparison to control RNA.

Example 2: EVs Derived from RIG-I-Stimulated Cells Express Enhanced Levels of the NKp30-Ligand BAG6

As RIG-has been described to activate different cells of the immune system, the inventors next analyzed whether RIG-induced EVs are taken up by immune cells. For this, the inventors analyzed the association of CFSE-labeled D04mel-derived EVs with immune cells within peripheral blood mononuclear cells (PBMC) by flow cytometry. In comparison to ctrl-EVs, RIG-I-EVs demonstrated significant higher association to NK cells arguing for enhanced binding or uptake of RIG-I-EV by this cell type (FIG. 2A). Even if there was slight increased association with CD3 positive cells as well, this was less pronounced than the association with NK cells.

To unravel possible phenotypic differences between ctrl and RIG-I-EVs, the inventors analyzed the expression levels of ligands for activating NK cell receptors on tumor-EVs (FIG. 2B) and the cell surface of tumor cells in response to 3pRNA. The expression of the NKG2D-ligands MICA, MICB, the UL binding proteins 1-3, the putative NKp46 ligand vimentin and the NKp30 ligand B7-H6 on tumor cells as well as EVs was not detectable or showed no difference irrespective of treatment (FIG. 2B). In contrast, the NKp30-ligand BAG6 was strongly induced on the surface of RIG-I-EVs but not on ctrl-EVs released from the melanoma cell line D04mel (FIG. 2B). In line with increased BAG6 expression on RIGI-EVs, recombinant NKp30-fc fusion protein bound stronger to RIG-I-EVs than ctrl-EVs (FIG. 2C). Compared to the EV surface (FIG. 2D right), the expression of BAG6 on tumor cells was weak with only slight increase in response to RIG-activation (FIG. 2D left). Equal expression level of CD9 on EVs between RIG-I-EVs and ctrl-EVs suggest that equal amounts of EVs were analyzed indicating that increased BAG6 expression on EVs does not simply reflect the cell surface but displays specific EV composition. The increased BAG6 expression on RIG-I-EVs was also detectable on EVs from different melanoma cell line (Ma-Mel-86c) (FIG. 2E). Knock down of RIG-I abolished the induction of BAG6 on RIG-I-EVs in response to 3pRNA treatment of the tumor cells confirming the specific role of RIG-I (FIG. 2F). RIG-activation did not lead to an upregulation of BAG6 mRNA expression in the D04mel cells (data not shown). This argues for regulation of BAG6 on protein level and/or for enhanced transport of BAG6 in the EVs. Taken together, the results indicate that RIG-activation leads to the release of BAG6-positive EVs.

Example 3: BAG6-Positive Tumor-EVs Derived from RIG-I-Stimulated Cells Activate NK Cells and Promote NKp30-Dependent Cytotoxicity Since BAG6 is described to activate NK cells, the inventors investigated the functional impact of the phenotypic differences between ctrl-EVs and RIG-I-EVs on the activation status of NK cells within PBMCs. Incubation with RIG-I-EVs led to an enhanced expression of the activation marker CD69 on NK cells within PBMCs (FIG. 3A) and on primary naive NK cells (FIG. 3B). The observed NK cell activation was mainly NKp30-mediated, since antibody-mediated blockade of NKp30 strongly reduced the RIG-I-EV-dependent induction of CD69 on primary naive NK cells (FIG. 3B). In addition, RIG-I-EVs derived from melanoma cells activated naive NK cells to lyse untreated melanoma cells (D04mel) (FIG. 3C). The inhibition of NKp30 function on NK cells (FIG. 3C) or BAG6 on melanoma-derived EVs (FIG. 3D) inhibited this effect. Thus, the data argue that EVs bind to and activate NK cells in BAG6/NKp30 dependent manner, leading to an enhanced tumor cell lysis in vitro.

Example 4: RIG-Induced Tumor-EVs Restrict Tumor Growth in Vivo

The inventors next analyzed the antitumor activity of RIG-I-EVs from melanoma cells in vivo. EVs were prepared from the melanoma cell line HCmel12 which is derived from the spontaneous HGF-CDK4 (R24C) melanoma mouse model and expressed vesicles marker CD81 and CD9. As shown for human EVs, RIG-I stimulation caused an upregulation of BAG6 on EVs derived from mouse melanoma cells (FIG. 4A). Furthermore, like their human counterparts, HCmel12-derived RIG-I-EVs increased CD69 expression on mouse NK cells significant stronger than ctrl-EVs ex vivo (FIG. 4B). RIG-I-EVs but not ctrl-EVs increased the expression of the activation marker CD69 on NK cells in draining lymph nodes (FIG. 4C) significantly, which is in line with the in vitro data. Next, HCmel12 cells were injected subcutaneously into the flank of C57BL/6 mice. After d established melanomas were treated by four intra-tumoral injections of EVs derived from RIG-I-stimulated or control HCmel12 melanoma cells (FIG. 4D). Treatment with RIG-I-EVs—but not with ctrl-EVs—effectively inhibited melanoma growth (FIG. 4E). This effect was NK cell dependent, since depletion of NK cells abrogated the antitumor effect mediated by RIG-I-EVs (FIG. 4E). Thus, EVs derived from RIG-stimulated tumor cells activate NK cells and suppress tumor growth of established tumors in vivo in NK cell-dependent manner.

Example 5: RIG-Induced Tumor-EVs Initiate the Production of Type I Interferons

In the following section the inventors figured out the potential of RIG-I induced tumor-EVs to induce cytokines or chemokines in different immune cell subsets. Therefore, EVs were prepared from human melanoma cells and stained with CFSE. Co-culture of RIG-I induced EVs but not of ctrl EVs induced a significant association of EVs with NK cells and especially monocytes (FIG. 5A). The mechanism of NK-activation by RIG-I induced EVs was evaluated above. Interestingly, monocytes showed upon co-culturing with RIG-I induced tumor EVs a strong upregulation of the activation marker CD86 (FIG. 5B). To evaluate whether the activation of immune cells is only due to activation markers or whether they also respond with the release of cytokines the inventors examined the potential of PBMCs to release different kind of inflammatory cytokines or chemokines. RIG-I induced tumor EVs were not able to induce inflammatory cytokines like IL1b, IL6, IL8, IL15 or TNFa. Contrary, type I Interferons, CXCL10 and IL-12p70 was induced (FIG. 5C+D). The induction of CXCL10 was dependent on the presence of CD14+ monocytes within the PBMC population since depletion of monocytes in PBMCs abrogated CXCL10 production by RIG-I-EVs (FIG. 5D). Beside RIG-I activation the inventors also figured out the potential of other immune activating ligands to transfer cytokine inducing potential by tumor-induced EVs. As shown in FIG. 5E, EVs derived from poly(I:C) or DNA-Ligands (Vac30, Vac50, Vac90) had the capability to induce CXCL10 in PBMCs as it is shown for 3pRNA induced EVs (FIG. 5E). To evaluate whether cytokine induction by RIG-I induced EVs can also be obtained in a physiological in vivo setting, murine derived RIG-I EVs were injected intravenously into mice and serum production of CXCL10 was determined after 3 h and 5 h hours (FIG. 5F). RIG-I-EVs were very potent to induce CXCl10 in vivo. Furthermore, even the injection of RIG-I induced EVs directly into the tumor led to the increase of CXCL10 mRNA level (FIG. 5G).

Example 6: RIG-I Induced Tumor EVs Transfer Functional RIG-I Ligands

In the next step the inventors wanted to figure out, what component of RIG-I EVs induce the production of antiinfective and anti-tumor cytokines. Therefore, they isolated the RNA of the EVs and transfected EV-derived RNA into PBMCs and monocytes. RIG-I induced EV RNA was able to induce type I interferons and CXCL10 in PBMCs as well as CXCL10 in monocytes indicating that the RNA of EVs is the active component inducing these specific cytokines. The production of type I Interferons and CXCL10 are typical signs for the activation of pattern recognition receptors. Since EVs were induced by the pattern recognition RIG-I the inventors concluded that an RIG-I ligand is transferred via EVs mediating the effect. To destroy the potential of the RIG-I ligand to activate RIG-I the inventors removed chemically the 3p-moiety of the RNA derived from RIG-I induced EVs. It can be shown in EV preparations derived from four different cell lines that all of them confer the ability to induce CXCL10 within PBMCs while the removal of the 3p-Moiety with FastAP abolished the cytokine induction (FIG. 6C). The inventors proofed that an RIG-I ligand is transferred via EVs and they confirmed the recognition of the RIG-I-EV RNA by RIG-I since the use of RIG-I knock out cell lines abolished the induction of CXCL10 completely (FIG. 6D). To figure out the role of RIG-I as receptor mediating the transfer of the RIG-I ligand into the EVs the inventors made use of RIG-I knock out cell lines. RIG-I induced EVs derived from RIG-I knock out cells had the same ability to induce CXCL10 in PBMCs compared to RIG-I-EVs derived from wildtype cells indicating that RIG-I is not involved in the transfer of the RIG-I ligand in EVs (FIG. 6E). FIGS. 6S1 and 6S2 are controls confirming the RIG-I knock out on protein level as well as on functional level and that reconstitution of RIG-I protein in knock out cells restores their wildtype behavior.

Example 7: RIG-I-Induced EVs Induce Dendritic Cells Maturation

In the next step the inventors investigated the potential of RIG-I induced EVs in antigen-presenting cells. They evaluated the ability of RIG-I induced EVs derived from five different primary melanoma cell lines (D05mel, Ma-Mel-86a, Ma-Mel-86b, Ma-Mel-86c and SK-Mel-29) to induce type I IFN and CXCL10 in dendritic cells. RIG-I induced tumor EVs derived from all investigated melanoma cell line showed the induction of type I IFN and CXCL10 compared to ctrl EVs (FIGS. 7A and 7B). The induction of CXCL10 is dependent on TBK1 which is involved in RIG-I signaling as inhibition of TBK1 by Bx795 partially diminished the induction of CXCL10 induced by RIG-I-EVs (FIG. 7C). Furthermore, while inhibiting Type I IFN signaling with B18R the induction of CXCL10 by RIG-I-EVs can be partially abolished as well (FIG. 7C). Activation of DCs by ctrl or RIG-I-EVs was determined by the measurement of CD80 by flow cytometry. RIG-I induced EVs derived from all investigated tumor cells stimulated the activation marker CD80 on DCs (FIG. 7D). The regulation of CD80 expression by RIG-I-EVs is dependent on TBK1 and type I IFN signaling, as inhibition by Bx795 or B18R partially inhibited CD80 expression (FIG. 7E). Besides the regulation of the maturation marker CD80 the inventors also determined other DC maturation molecules like CD83 and CD86. RIG-I induced EVs but not ctrl EVs induced the expression of CD83 (FIG. 7G) and CD86 (FIG. 7F) on DCs.

Example 8: Transfer of RIG-I Ligands and Tumor Antigens in EVs Promote Antigen-Specific T Cell Responses Beside DCs maturation the inventors observed the production of IL12p70 by RIG-I induced EVs but not by ctrl EVs in DCs, depending completely on TBK1 as well as Type I IFN signaling as inhibition with respective antibodies completely abolished the production of IL12p70 (FIG. 8A). Interestingly, the induction of IL12p70 was not inducible by the transfection of the RIG-I ligand with commercial available transfection reagents while CXCL10 was inducible (FIG. 8B). To figure out, whether tumor-antigen is transferred into EVs the inventors evaluated the expression of Melan A in the investigated tumor cells. Beside Ma-Mel-66a, Melan A is expressed in all investigated tumor cells lines (FIG. 8C). According to the Melan A expression in the investigated cells, EVs derived of these cells showed same expression pattern of Melan A (FIG. 8D). Finally, the inventors characterized the potential of RIG-I induced EVs for antigen-specific T-cell activation. Antigen-specific T cell responses induced by RIG-I-EVs was determined by human IFNg ELISPOT Assay. HLA-A2 positive DCs were incubated with ctrl-EVs or RIG-I-EVs and melan A (upper panel) or tyrosinase (bottom panel) sensitive autologous T cell clones were added and production of IFNg was monitored. Assay performance was controlled while using only T cells, DCs with no loading of EVs in the presence of T cells (DCs+T cells) and incubation of T cells with D05mel melanoma cells (T cells+Melanoma cells) as positive control. RIG-I induced EVs were potent inducers of IFNg production by melan a and tyrosinase responsive T cells compared to ctrl EVs (FIG. 8E).

The invention claimed is:

1. A method for the production of extracellular vesicles, the method comprising the steps of
   (a) Culturing a tumor cell, an epithelial cell, or a fibroblast,
   (b) Bringing into contact the tumor cell, the epithelial cell, or the fibroblast with at least one ligand of an innate immunity receptor in an amount and time sufficient for the tumor cell, the epithelial cell, or the fibroblast to release extracellular vesicles with an anti-infective and/or anti-tumor activity and/or immune stimulatory activity,
   (c) Isolating and/or purifying the released extracellular vesicles.

2. The method according to claim 1, wherein the anti-infective and/or anti-tumor activity and/or immune stimulatory activity involves an activity of inducing cytokine production, and/or an activity of the extracellular vesicles to activate immune cells, such as monocytes, natural killer (NK) cells and/or T cells.

3. The method according to claim 1, wherein the at least one ligand of an innate immunity receptor is selected from the group consisting of ligand of retinoic acid-inducible gene I (RIG-I), ligand of melanoma differentiation antigen 5 (MDA5) and ligand of cyclic GMP-AMP synthase (cGAS); and preferably is an RNA molecule, such as 3pRNA, a DNA molecule, such as Y-form DNA, or is polyinosinic:polycytidylic acid poly (I:C).

4. The method according to claim 1, wherein the at least one innate immunity receptor is retinoic acid-inducible gene I (RIG-I), melanoma differentiation antigen 5 (MDA5) and/or is cyclic GMP-AMP synthase (cGAS).

5. The method according to claim 1, wherein isolating and/or purifying comprises a step of determining the presence of BAG6 on the extracellular vesicles.

6. The method according to claim 1, wherein step (b) comprises bringing into contact the tumor cell, the epithelial cell, or the fibroblast with at least two ligands of an innate immunity receptor selected from the group consisting of an RNA molecule, such as 3pRNA, a DNA molecule, such as Y-form DNA, and polyinosinic:polycytidylic acid poly (I:C); and wherein the at least two ligands of an innate immunity receptor are two ligands of two different innate immunity receptors.

7. The method according to claim 1, wherein step (b) comprises bringing into contact the tumor cell, the epithelial cell, or the fibroblast with at least three ligands of an innate immunity receptor selected from the group consisting of an RNA molecule, such as 3pRNA, a DNA molecule, such as Y-form DNA, and polyinosinic:polycytidylic acid poly (I:C); and wherein the at least three ligands of an innate immunity receptor are three ligands of three different innate immunity receptors.

8. A method of producing a medicament for treating a disease in a patient, the method comprising the steps of
   (a) Providing a tumor cell, an epithelial cell or a fibroblast,
   (b) Performing with the tumor cell, the epithelial cell or the fibroblast the method according to claim 1, to obtain released extracellular vesicles with anti-infective and/or anti-tumor activity and/or immune stimulatory activity,
   (c) Formulating a medicament with the released anti-tumor extracellular vesicles for treating a disease in a patient.

9. The method according to claim 8, wherein the tumor cell, the epithelial cell or the fibroblast is derived from a cellular sample of a patient to be treated, and wherein the formulated medicament is for treating said patient.

10. The method according to claim 9, wherein the tumor cell, the epithelial cell or the fibroblast is not derived from the patient to be treated.

11. The method according to claim 9, wherein the disease is cancer, and wherein the cell is a tumor cell; or wherein the disease is a viral disease, and wherein the cell is the fibroblast.

* * * * *

SEQUENCE LISTING

<160> NUMBER OF SEQ ID NOS: 9

<210> SEQ ID NO 1
<211> LENGTH: 76
<212> TYPE: DNA
<213> ORGANISM: artificial
<220> FEATURE:
<223> OTHER INFORMATION: primer

<400> SEQUENCE: 1
gggacgctga cccagaagat ctactatttc tagtagatct tctgggtcag cgtccctata    60
gtgagtcgta ttacaa    76

<210> SEQ ID NO 2
<211> LENGTH: 76

```
<212> TYPE: DNA
<213> ORGANISM: artificial
<220> FEATURE:
<223> OTHER INFORMATION: primer

<400> SEQUENCE: 2
ttgtaatacg actcactata gggacgctga cccagaagat ctactagaaa tagtagatct      60
tctgggtcag cgtccc                                                     76

<210> SEQ ID NO 3
<211> LENGTH: 30
<212> TYPE: DNA
<213> ORGANISM: artificial
<220> FEATURE:
<223> OTHER INFORMATION: primer

<400> SEQUENCE: 3
gggatgagta aaggagaaga acttttaggg                                      30

<210> SEQ ID NO 4
<211> LENGTH: 30
<212> TYPE: DNA
<213> ORGANISM: artificial
<220> FEATURE:
<223> OTHER INFORMATION: primer

<400> SEQUENCE: 4
gggtaaaagt tcttctcctt tactcatggg                                      30

<210> SEQ ID NO 5
<211> LENGTH: 50
<212> TYPE: DNA
<213> ORGANISM: artificial
<220> FEATURE:
<223> OTHER INFORMATION: primer

<400> SEQUENCE: 5
gggatgagta aaggagaaga acttttcact ggagttatcc cagttatggg                50

<210> SEQ ID NO 6
<211> LENGTH: 50
<212> TYPE: DNA
<213> ORGANISM: artificial
<220> FEATURE:
<223> OTHER INFORMATION: primer

<400> SEQUENCE: 6
gggataactg gataactcc agtgaaaagt tcttctcctt tactcatggg                 50

<210> SEQ ID NO 7
<211> LENGTH: 90
<212> TYPE: DNA
<213> ORGANISM: artificial
<220> FEATURE:
<223> OTHER INFORMATION: primer

<400> SEQUENCE: 7
gggatgagta aaggagaaga acttttcact ggagttatcc cagttattgt tgaattagat     60
ggcgatgtta atgggcaaaa attctctggg                                      90

<210> SEQ ID NO 8
<211> LENGTH: 90
<212> TYPE: DNA
<213> ORGANISM: artificial
<220> FEATURE:
```

```
<223> OTHER INFORMATION: primer

<400> SEQUENCE: 8
gggagagaat ttttgcccat taacatcgcc atctaattca acaataactg ggataactcc        60
agtgaaaagt tcttctcctt tactcatggg                                         90

<210> SEQ ID NO 9
<211> LENGTH: 23
<212> TYPE: DNA
<213> ORGANISM: artificial
<220> FEATURE:
<223> OTHER INFORMATION: gRNA

<400> SEQUENCE: 9
gggtcttccg gatataatcc tgg                                                23
```